United States Patent
Cheesman et al.

(10) Patent No.: US 11,576,846 B2
(45) Date of Patent: Feb. 14, 2023

(54) EMULSION STABILISER

(71) Applicant: AQDOT LIMITED, Cambridge (GB)

(72) Inventors: Benjamin Cheesman, Cambridge (GB); Roger Coulston, Cambridge (GB); Andrew Howe, Cambridge (GB); Jennifer Efua Kwansima Quansah, Cambridge (GB); Michael Pedder, Cambridge (GB)

(73) Assignee: AQDOT LIMITED, Cambridge (GB)

( * ) Notice: Subject to any disclaimer, the term of this patent is extended or adjusted under 35 U.S.C. 154(b) by 54 days.

(21) Appl. No.: 17/040,325

(22) PCT Filed: Mar. 22, 2019

(86) PCT No.: PCT/GB2019/050827
§ 371 (c)(1),
(2) Date: Sep. 22, 2020

(87) PCT Pub. No.: WO2019/180458
PCT Pub. Date: Sep. 26, 2019

(65) Prior Publication Data
US 2021/0022968 A1    Jan. 28, 2021

(30) Foreign Application Priority Data

Mar. 22, 2018 (GB) .................................. 1804634
Apr. 16, 2018 (GB) .................................. 1806167

(51) Int. Cl.
*A61K 8/06*    (2006.01)
*A61K 8/49*    (2006.01)
*A61K 8/73*    (2006.01)
*A61Q 19/00*   (2006.01)

(52) U.S. Cl.
CPC .............. *A61K 8/062* (2013.01); *A61K 8/494* (2013.01); *A61K 8/732* (2013.01); *A61K 8/738* (2013.01); *A61Q 19/00* (2013.01); *A61K 2800/10* (2013.01); *A61K 2800/52* (2013.01); *A61K 2800/5428* (2013.01)

(58) Field of Classification Search
CPC ........ A61K 8/062; A61K 8/494; A61K 8/732; A61K 8/738; A61K 2800/10; A61K 2800/52; A61K 2800/5428; A61K 8/06; A61K 8/49; A61K 8/73; A61K 8/737; A61Q 19/00

See application file for complete search history.

(56) References Cited

U.S. PATENT DOCUMENTS

2006/0251725 A1* 11/2006 Kim .................... C07D 487/22
                                                    514/393
2016/0303052 A1* 10/2016 Fahmy ................. A61K 38/217

FOREIGN PATENT DOCUMENTS

| GB | 2 556 619 A    | 6/2018  |
|----|----------------|---------|
| WO | 00/33806 A1    | 6/2000  |
| WO | 2007/091016 A1 | 8/2007  |
| WO | 2008/003685 A1 | 1/2008  |
| WO | 2013/124654 A1 | 8/2013  |
| WO | 2016/156289 A1 | 10/2016 |
| WO | 2017/141029 A1 | 8/2017  |
| WO | 2018/037209 A1 | 3/2018  |

OTHER PUBLICATIONS

Isaacs et al.; "The Cucurbit[n]uril Family;" Angewandte Chemie; 2005; pp. 4844-4870; vol. 44.
May 22, 2019 Search Report issued in International Patent Application No. PCT/GB2019/050827.
May 22, 2019 Written Opinion of the International Searching Authority issued in International Patent Application No. PCT/GB2019/050827.
Nov. 5, 2018 Search Report issued in British Patent Application No. GB1804634.2.

* cited by examiner

*Primary Examiner* — Robert A Wax
*Assistant Examiner* — Quanglong N Truong
(74) *Attorney, Agent, or Firm* — Oliff PLC

(57) ABSTRACT

A dispersion stabiliser precursor composition including one or more of cucurbituril, a variant or a derivative thereof, and one or more oil-in-water macromolecular amphiphilic emulsifier, wherein the composition is in the form of a free flowing powder; and an oil-in-water emulsion composition including one or more of cucurbituril, a variant or a derivative thereof, and one or more oil-in-water macromolecular amphiphilic emulsifier.

18 Claims, 17 Drawing Sheets

EMULSION STABILISER

This invention provides a dispersion stabiliser precursor composition comprising cucurbituril and one or more hydrophobically-modified polysaccharides, wherein the composition is in the form of a free flowing powder. The invention also provides an oil-in-water emulsion composition comprising cucurbituril and one or more hydrophobically-modified polysaccharides.

Oil-in-water emulsions comprising high levels of dispersed phase are known to the art. However, such dispersions usually require large levels of hydrophilic surfactants, which may not be desirable in many applications. For example, in the personal care field, such surfactants may provoke skin reactions, such as redness or itching, or may confer undesired dryness to the skin. They are also known to reduce the water resistance of coatings and adhesives.

The diameter of oil droplets in oil-in-water emulsions is usually limited to 10 microns because of the tendency of larger droplets to cream, sediment or coalesce, leading to emulsion destabilization. In many applications, however, larger droplet sizes may have some advantages, such as improved bioavailability of the emulsified oils and active ingredients dissolved therein, and enhanced emulsion breakability under shear stresses, for example in agricultural or printing applications.

Associative polymers, for example hydroxypropyl methylcellulose or acrylic acid polymers such as Carbomer, provide stable emulsions that can be prepared by cold processing. However, associative polymers may increase the viscosity of emulsions and impact negatively on their flow behaviour. Furthermore, emulsions stabilized with too high levels of such polymers may have long drying times and a sticky feel, especially when biopolymers, such as polysaccharides, are used.

Typically, however, stable, high internal phase emulsions, such as oil-in-water emulsions having high levels of oils, for example higher than 30% w/v, require using synthetic polymers as stabilizing systems. Many of these polymers are sensitive to pH, such as for example those comprising acrylic acid groups, or to temperature, such as those comprising ethoxylated moieties.

An appropriate balance between stability and flowability is not easy to achieve mainly because conventional stabilising networks have too strong interactions making them too viscoelastic. WO 2008/003685 (Henkel KGAA) relates to oil-in-water emulsions which contain at least one cyclodextrin or cyclodextrin derivative, at least one hydrophobically modified polysaccharide, at least one fatty substance and water. The invention also relates to the use of said emulsions in cosmetic or pharmaceutical compositions. The said emulsions may also contain particulates or pigments, for example to provide coloration or protection from UV radiation.

WO 2013/124654 (Cambridge Enterprise Limited) relates to a hydrogel, wherein the hydrogel has a supramolecular cross-linked network obtainable or obtained from the complexation of an aqueous composition comprising a host, such as cucurbituril, and one or more polymers having suitable guest functionality. One or more polymers in the aqueous composition may have a molecular weight of 50 kDa or more, such as 200 kDa or more. The hydrogel may hold a component, such as a therapeutic compound or a biological molecule. The hydrogels are suitable for use in medicine.

SUMMARY OF THE INVENTION

In a first aspect of the invention, a dispersion stabiliser precursor composition is provided, the dispersion stabiliser precursor composition comprising one or more of cucurbituril, a variant or a derivative thereof, and one or more oil-in-water macromolecular amphiphilic emulsifier, wherein the composition is in the form of a free flowing powder.

In a second aspect of the invention, an oil-in-water emulsion composition is provided, the oil-in-water emulsion composition comprising one or more of cucurbituril, a variant or a derivative thereof, and one or more oil-in-water macromolecular amphiphilic emulsifier.

The term "macromolecular" means a polymer having at least 10, preferably at least 15 repeat units.

In a third aspect of the invention, a method for preparing an oil-in-water emulsion composition according to the second aspect of the invention is provided, the method comprising the steps of:

(a) preparing an aqueous phase;
(b) preparing an oil phase;
(c) combining the aqueous and oil phases under shear;
wherein the one or more of cucurbituril, a variant or a derivative thereof, and one or more oil-in-water macromolecular amphiphilic emulsifier is added to the oil phase and/or the aqueous phase.

In a fourth aspect of the invention, use of the dispersion stabiliser precursor composition according to the first aspect of the invention for stabilising an oil-in-water emulsion is provided. The said emulsions are well suited to applications in the field of cosmetics or personal care and may also contain dispersed solid phase.

BRIEF DESCRIPTION OF THE FIGURES

The invention is illustrated with reference to the following Figures in which.

Figure 1:
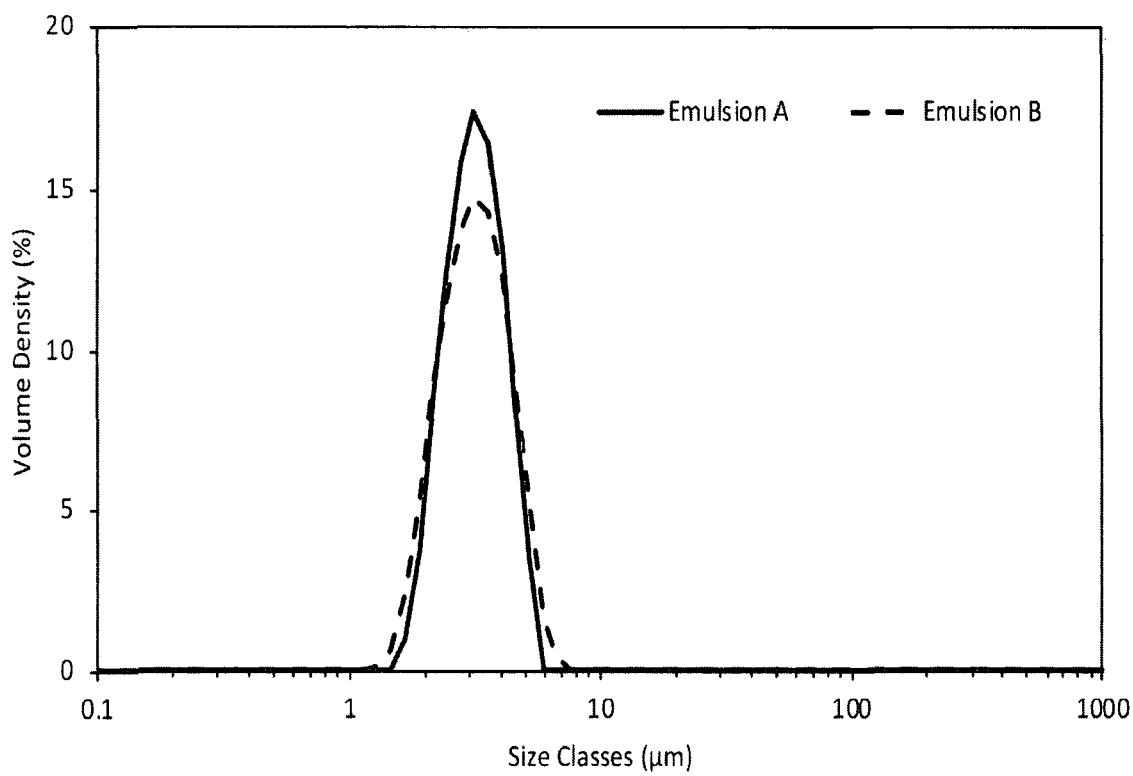
FIG. 1 shows the droplet size volume weighted distribution for emulsions containing the dispersion stabiliser of the invention (Emulsion A) and OSA-starch alone (Emulsion B) within 1 hour of preparation.

The term CB[n] refers to a mixture of 0-15% w/w CB[5], 50-60% w/w CB[6], 25-35% w/w CB[7] and 5-15% w/w CB[8], wherein the term CB[5], CB[6], CB[7] and CB[8] refer to cucurbituril with 5, 6, 7, and 8 glycoluril units respectively.

DETAILED DESCRIPTION OF THE INVENTION

In a first aspect of the invention, a dispersion stabiliser precursor composition is provided, the dispersion stabiliser precursor composition comprising one or more of cucurbituril, a variant or a derivative thereof, and one or more oil-in-water macromolecular amphiphilic emulsifier, wherein the composition is in the form of a free flowing powder.

In a second aspect of the invention, an oil-in-water emulsion composition is provided, the oil-in-water emulsion composition comprising one or more of cucurbituril, a variant or a derivative thereof, and one or more oil-in-water macromolecular amphiphilic emulsifier.

Such oil-in-water compositions are preferably used in the personal care field, for example, for use on skin. Specific examples of skin care compositions includes moisturisers, barrier creams, sunscreens, self-tanning compositions, make-up compositions, and night creams.

Cucurbituril is a member of the cavitand family, and the general cucurbituril structure is based on the cyclic arrangement of glycoluril subunits linked by methylene bridges.

The preparation and purification of cucurbituril compounds is well described in the art, for example, Lagona et al. ("The cucurbit[n]uril family" Angew. Chem. Int. Ed., 44, 4844 (2005)) review the synthesis and properties of cucurbituril compounds, including derivatives, analogues and congener within the cucurbituril family.

For example, cucurbit[8]uril (CB[8]; CAS 259886-51-6) is a barrel shaped container molecule which has eight repeat glycoluril units and an internal cavity size of $479Å^3$ (see structure below). CB[8] is readily synthesised using standard techniques and is available commercially (e.g. Sigma-Aldrich, MO USA).

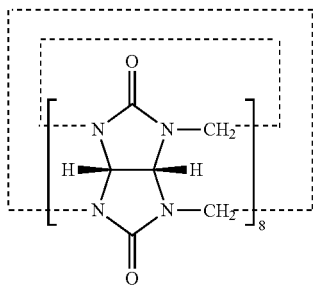

In one embodiment, the cucurbituril is selected from the group consisting of CB[5], CB[6], CB[7], CB[8], CB[9], CB[10], CB[11], CB[12], CB[13], CB[14] and mixtures thereof. In one embodiment, the cucurbituril is selected from the group consisting of CB[5], CB[6], CB[7], CB[8], CB[9], CB[10], CB[11], CB[12] and mixtures thereof. In one embodiment, the cucurbituril is selected from the group consisting of CB[5], CB[6], CB[7], CB[8] and mixtures thereof. In one embodiment, the cucurbituril is CB[6]. In one embodiment, the cucurbituril is CB[7]. In one embodiment, the cucurbituril is CB[8].

A variant of cucurbituril may include a structure having one or more repeat units that are structurally analogous to glycoluril. The repeat unit may include an ethylurea unit. Where all the units are ethylurea units, the variant is a hemicucurbituril. The variant may be a hemicucurbit[12]uril (shown below, see also Lagona et al.).

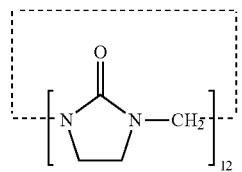

A derivative of a cucurbituril is a structure having one, two, three, four or more substituted glycoluril units. A substituted cucurbituril compound may be represented by the structure below:

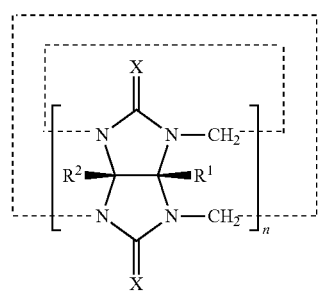

wherein:

n is an integer of at least 5;

and for each glycoluril unit:

each X is O, S or $NR^3$, and

—$R^1$ and —$R^2$ are each independently selected from —H and the following optionally substituted groups: —$R^3$, —OH, —$OR^3$, —COOH, —$COOR^3$, —$NH_2$, —$NHR^3$ and —$N(R^3)_2$ where —$R^3$ is independently selected from $C_{1-20}$ alkyl, $C_{6-20}$ carboaryl, and $C_{5-20}$ heteroaryl, or where —$R^1$ and/or —$R^2$ is —$N(R^3)_2$, both —$R^3$ together form a $C_{5-7}$ heterocyclic ring; or together —$R^1$ and —$R^2$ are $C_{4-6}$ alkylene forming a $C_{6-8}$ carbocyclic ring together with the uracil frame.

In one embodiment, one of the glycoluril units is a substituted glycoluril unit. Thus, —$R^1$ and —$R^2$ are each independently —H for n–1 of the glycoluril units. In one embodiment, n is 5, 6, 7, 8, 9, 10, 11, 12, 13 or 14. In one embodiment, n is 5, 6, 7, 8, 9, 10, 11 or 12. In one embodiment, n is 5, 6, 7, 8, 10, 12 or 14. In one embodiment, n is 5, 6, 7, 8, 10 or 12. In one embodiment, n is 5, 6, 7 or 8. In one embodiment, n is 6. In one embodiment, n is 7. In one embodiment, n is 8.

In one embodiment, each X is O. In one embodiment, each X is S.

In one embodiment, $R^1$ and $R^2$ are each independently H.

In one embodiment, for each unit one of $R^1$ and $R^2$ is H and the other is independently selected from —H and the following optionally substituted groups: —$R^3$, —OH, —$OR^3$, —COOH, —$COOR^3$, —$NH_2$, —$NHR^3$ and —$N(R^3)_2$. In one embodiment, for one unit one of $R^1$ and $R^2$ is H and the other is independently selected from —H and the following optionally substituted groups: —$R^3$, —OH, —$OR^3$, —COOH, —$COOR^3$, —$NH_2$, —$NHR^3$ and —$N(R^3)_2$. In this embodiment, the remaining glycoluril units are such that $R^1$ and $R^2$ are each independently H.

Preferably —$R^3$ is $C_{1-20}$ alkyl, most preferably $C_{1-6}$ alkyl. The $C_{1-20}$ alkyl group may be linear and/or saturated. Each group —$R^3$ may be independently unsubstituted or substituted. Preferred substituents are selected from: —$R^4$, —OH, —$OR^4$, —SH, —$SR^4$, —COOH, —$COOR^4$, —$NH_2$, —$NHR^4$ and —$N(R^4)_2$, wherein —$R^4$ is selected from $C_{1-20}$ alkyl, $C_{6-20}$ carboaryl, and $C_{5-20}$ heteroaryl. The substituents may be independently selected from —COOH and —$COOR^4$.

In some embodiments, —$R^4$ is not the same as —$R^3$. In some embodiments, —$R^4$ is preferably unsubstituted.

Where —$R^1$ and/or —$R^2$ is —$OR^3$, —$NHR^3$ or —$N(R^3)_2$, then —$R^3$ is preferably $C_{1-6}$ alkyl. In some embodiments, —$R^3$ is substituted with a substituent —$OR^4$, —$NHR^4$ or —$N(R^4)_2$. Each —$R^4$ is $C_{1-6}$ alkyl and is itself preferably substituted.

The oil-in-water macromolecular amphiphilic emulsifier is preferably a hydrophobically-modified polysaccharide.

The hydrophobically-modified polysaccharide may be a polysaccharide which has been modified by reaction with $C_1$-$C_{22}$ alkyl- or a $C_3$-$C_{22}$ alkenyl-succinic anhydride, preferably octenyl succinic anhydride.

The hydrophobically-modified polysaccharide may be a hydrophobically-modified branched polysaccharide, preferably the branched polysaccharide is selected from the group consisting of starch, amylopectin, dextrin, gum Arabic, and mixtures thereof, and preferably the hydrophobically-modified polysaccharide is octenyl succinic anhydride modified starch or gum Arabic.

Preferably the weight ratio of one or more of cucurbituril, a variant or a derivative thereof to one or more oil-in-water macromolecular amphiphilic emulsifier is 1:1000 to 1:5, preferably 1:500 to 1:7, most preferably 1:100 to 1:8.

The dispersion stabiliser precursor composition according to the first aspect of the invention or the oil-in-water emulsion composition according to the second aspect of the invention preferably are substantially free of a first surfactant which is water-soluble and/or has an HLB value of at least 12, preferably 12.5-20, most preferably 13-20. One advantage of this embodiment is that such an oil-in-water emulsion composition can be expected to not disrupt the barrier lipid bilayers and thus minimise damage of sensitive skin.

The term "substantially free" means, for the purposes of this specification, less than 0.5, preferably less than 0.05, more preferably less than 0.005% w/v of any oil-in-water emulsion composition comprising the dispersion stabiliser precursor composition according to the first aspect of the invention or the oil-in-water emulsion composition according to the second aspect of the invention.

Thus the level of first surfactant in the dispersion stabiliser precursor composition according to the first aspect of the invention is such as to produce in any oil-in-water emulsion composition comprising the dispersion stabiliser precursor composition a concentration of first surfactant which is less than 0.5, preferably less than 0.05, more preferably less than 0.005% w/v.

The dispersion stabiliser precursor composition according to the first aspect of the invention or the oil-in-water emulsion composition according to the second aspect of the invention preferably comprises a second surfactant which is oil-soluble and/or has an HLB value of 1-10, preferably 2-9.5, most preferably 3-9.5. It has been observed that inclusion of such a second surfactant assists dissolution of the hydrophobically-modified polysaccharide. The second surfactant is preferably selected from the group consisting of sorbitan monolaurate (HLB 8.6), sodium isostearoyl lactylate (Corbion Esterlac Care+, HLB 5.9), an alkali metal salt of stearoyl lactylate, and mixtures thereof. An example of a preferred alkali metal salt of stearoyl lactylate is sodium stearoyl lactylate.

Preferably the second surfactant is in the range 0.01-5, preferably 0.01-2% w/v of an oil-in-water emulsion composition comprising the dispersion stabiliser precursor composition of the first aspect of the invention or the oil-in-water emulsion composition of the second aspect of the invention. Thus the level of second surfactant in the dispersion stabiliser precursor composition of the first aspect of the invention is such as to produce when incorporated in any oil-in-water emulsion composition a concentration in the range 0.01-5, preferably 0.01-2% w/v.

The oil-in-water emulsion composition according to the second aspect of the invention preferably comprises 0.01-30, more preferably 0.05-20, most preferably 0.3-5% w/w combination of one or more of cucurbituril, a variant or a derivative thereof, and one or more oil-in-water macromolecular amphiphilic emulsifier.

The oil-in-water emulsion composition according to the second aspect of the invention preferably comprises 1-90, more preferably 2-75, most preferably 5-50% v/v an oil phase. The oil phase, in the form of droplets, may have a d90 of 0.1-1000, preferably 1-150, most preferably 4-110 microns in diameter.

The term "d90" means, for the purposes of the specification, the point in the size distribution up to and including which 90% of the total volume of material in the sample is 'contained'.

In a third aspect of the invention, a method for preparing an oil-in-water emulsion composition according to the second aspect of the invention is provided, the method comprising the steps of:
 (a) preparing an aqueous phase;
 (b) preparing an oil phase;
 (c) combining the aqueous and oil phases under shear;
 wherein the one or more of cucurbituril, a variant or a derivative thereof, and one or more oil-in-water macromolecular amphiphilic emulsifier is added to the oil phase and/or the aqueous phase.

The second surfactant, when used, may be added to the oil phase and/or the aqueous phase.

In a fourth aspect of the invention, use of the dispersion stabiliser precursor composition according to the first aspect of the invention for stabilising an oil-in-water emulsion is provided.

EXAMPLE 1

Comparative Study on the Stability of Oil-In-Water Emulsion With and Without The Dispersion Stabiliser of the Invention An 8% w/w solution of an octenylsuccinic anhydride (OSA) modified starch (herein referred to as OSA-starch (Purity Gum Ultra, Ingredion Incorporated unless otherwise indicated)) was prepared by adding 40.00 g of OSA-starch to 460.01 g deionised water. The mixture was then stirred overnight and then warmed to 80° C. until clear (about 2 hours). 200.0 g of this solution was then decanted and 0.101 g of potassium sorbate added.

This and the succeeding Examples used a mixture of cucurbiturils (hereinafter referred to as CB[n]) consisting of 0-15% w/w CB[5], 50-60% w/w CB[6], 25-35% w/w CB[7] and 5-15% w/w CB[8].

A solution of 8.88% w/w dispersion stabiliser (a blend of 9:1 w/w OSA-starch:CB[n]) was prepared by adding 40.000 g of OSA-starch to 4.444 g of CB[n] and 455.558 g of water. The mixture was stirred overnight and warmed at 80° C. for 2 hours. 100.0 g of this solution was then decanted and 0.049 g of potassium sorbate added.

A solution of 0.02% w/w Oil Red O (Alfa Aesar) in caprylyl methicone (Dow Corning) was prepared.

Emulsion A was prepared by preparing an aqueous phase through combining 7.50 mL of 8.88% w/w dispersion stabiliser with 15.00 mL of deionised water and mixed for 5 minutes at 5,000 rpm on a Silverson L5 High Shear Laboratory Mixer with small shearing head (a ⅝" micro general purpose disintegrating head). The oil phase was 8.57 mL caprylyl methicone containing 0.02% Oil Red O. The oil phase was added was then added to the aqueous phase and mixed at 10,000 rpm for 20 minutes to form Emulsion A comprising 2.22% w/w dispersion stabiliser which contained 2.0% w/w OSA-starch.

Emulsion B was prepared by preparing an aqueous phase by combining 7.50 mL of 8% w/w OSA-starch with 15.00 mL of deionised water and mixed for 5 minutes at 5,000 rpm on a Silverson L5 High Shear Laboratory Mixer with small shearing head (a ⅝" micro general purpose disintegrating head). To this aqueous phase, 8.57 mL caprylyl methicone was added and mixed at 10,000 rpm for 20 minutes to form Emulsion B comprising 2.0% w/w OSA-starch.

The droplet size distribution was measured using a Malvern Mastersizer 3000 with a HydroSV measuring cell containing water. A sample of the emulsion was added dropwise to the cell to a level that gives an obscuration of less than 20%. A series of individual measurements of size distribution were made and the average values calculated. The distributions are reported as the proportion of material by volume as a function of particle diameter. Typically, the distributions are of 3 samplings, each of which was measured 8 times (sub runs), corresponding to 24 individual measurements. The distributions are reported by volume and may be characterised by the parameters d50 (the midpoint) and d10 and d90 (the range). The parameter d10 signifies the point in the size distribution up to and including which 10% of the total volume of material in the sample is 'contained' and so describes the small-size end of the distribution, that describing the middle of the distribution is d50, while the large-size portion is described by d90 (90% of the volume of the particles).

Figure 2:
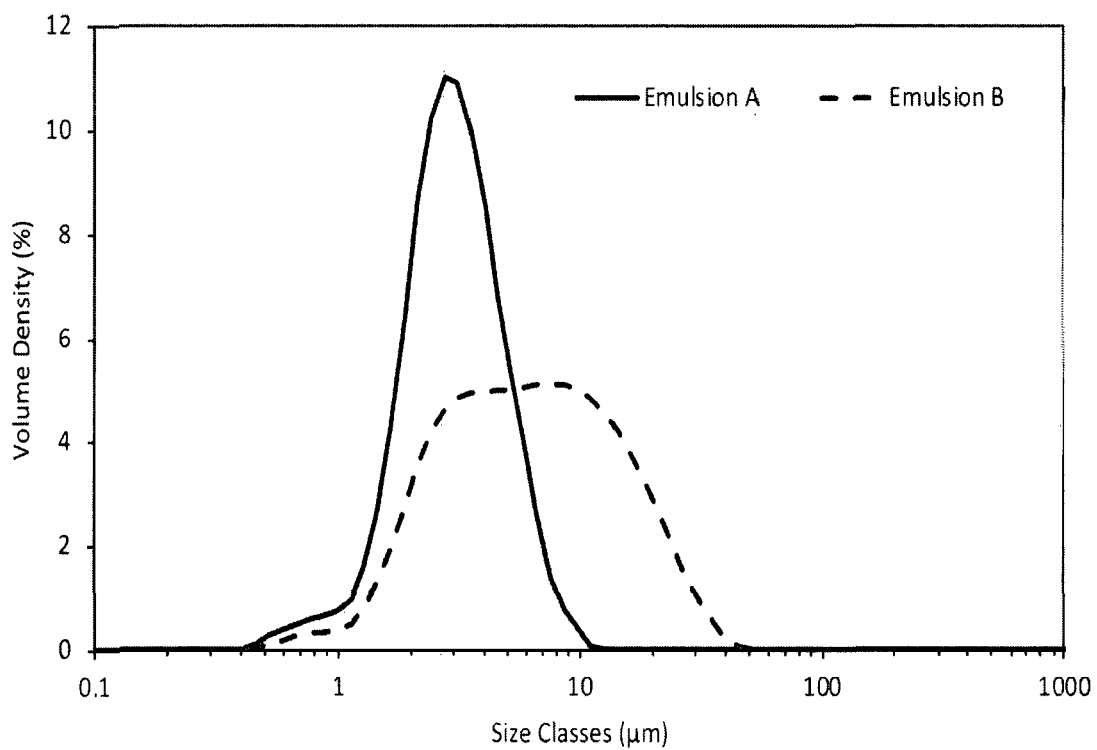
FIG. 2 shows the droplet size volume weighted distribution for emulsions containing the dispersion stabiliser of the invention (Emulsion A) and OSA-starch alone (Emulsion B) after storage for 1 week at 45° C.

FIG. 1 shows the size distributions of the two emulsions (within an hour of preparation). The size distributions of the two emulsions are very similar. The emulsions were then stored at 45° C. for 1 week and the particle size distribution measured again. The results are shown in FIG. 2 from which it is apparent that there has been very little change in the droplet size distribution for Emulsion A. In contrast the distribution of sizes for Emulsion B has moved to higher diameter.

The values for d10, d50 and d90 for each emulsion 1 hour after preparation and after 1 week at 45° C. are presented in Table 1Table 1. The growth in size with time is clearly seen in the increase in d50 and d90 for Emulsion B.

TABLE 1 d10, d50 and d90 droplet size for Emulsions A and B 1 hour after preparation and after 1 week at 45° C.

| Sample | | Initial | 1 Week |
|---|---|---|---|
| Emulsion A | d10 (μm) | 2.32 | 1.72 |
| | d50 (μm) | 3.34 | 3.15 |
| | d90 (μm) | 4.72 | 5.79 |
| Emulsion B | d10 (μm) | 2.18 | 2.21 |
| | d50 (μm) | 3.34 | 6.55 |
| | d90 (μm) | 5.01 | 19.6 |

On storage at 45° C., gross oil separation was seen from Emulsion B after 1 week (emulsion phase occupied just 55% of the total volume), while in contrast Emulsion A appeared to show no coalescence by visual observation (emulsion phase occupied 100% of the total volume) until between 1 and 5 weeks had passed. Thus this example demonstrates that emulsions prepared with dispersion stabiliser consisting of a blend of 9:1 w/w OSA-starch:CB[n] in accordance with the invention have greater stability to coalescence than emulsions prepared with the same concentration of the same OSA-starch.

EXAMPLE 2

Effect of Xanthan on Creaming of an Emulsion Comprising OSA-Starch or the Dispersion Stabiliser of Example 1

Solutions of 8% w/w OSA-starch and 8.88% w/w dispersion stabiliser and a solution of 0.02% w/w Oil Red O in caprylyl methicone were prepared as described in Example 1.

A solution of 1% w/w xanthan gum was prepared by adding 2.00 g xanthan gum to 198.01 g deionised water slowly with stirring. 0.10 g potassium sorbate was then added to the solution.

The aqueous phase of Emulsion C was prepared by combining 7.50 mL of 8.88% w/w dispersion stabiliser with 3.75 mL of 1% w/w xanthan gum solution and 11.25 mL deionised water and mixing for 5 minutes at 5,000 rpm on a Silverson L5 High Shear Laboratory Mixer with a small head (a ⅝" micro general purpose disintegrating head). To this aqueous phase, 8.65 mL Oil Red O containing caprylyl methicone was added and mixed at 10,000 rpm for 20 minutes to form Emulsion C comprising 2.22% w/w dispersion stabiliser (which contains 2.0% w/w OSA-starch) and 0.125% w/w xanthan gum.

The aqueous phase of Emulsion D was prepared by combining 7.50 mL of 8% w/w OSA-starch with 3.75 mL of 1% w/w xanthan gum solution and 11.25 mL of deionised water and mixing for 5 minutes at 5,000 rpm on a Silverson L5 High Shear Laboratory Mixer with small head (a ⅝" micro general purpose disintegrating head). To this aqueous phase, 8.65 mL Oil Red O containing caprylyl methicone was added and mixed at 10,000 rpm for 20 minutes to form Emulsion D comprising 2.0% w/w OSA-starch.

Figure 3:
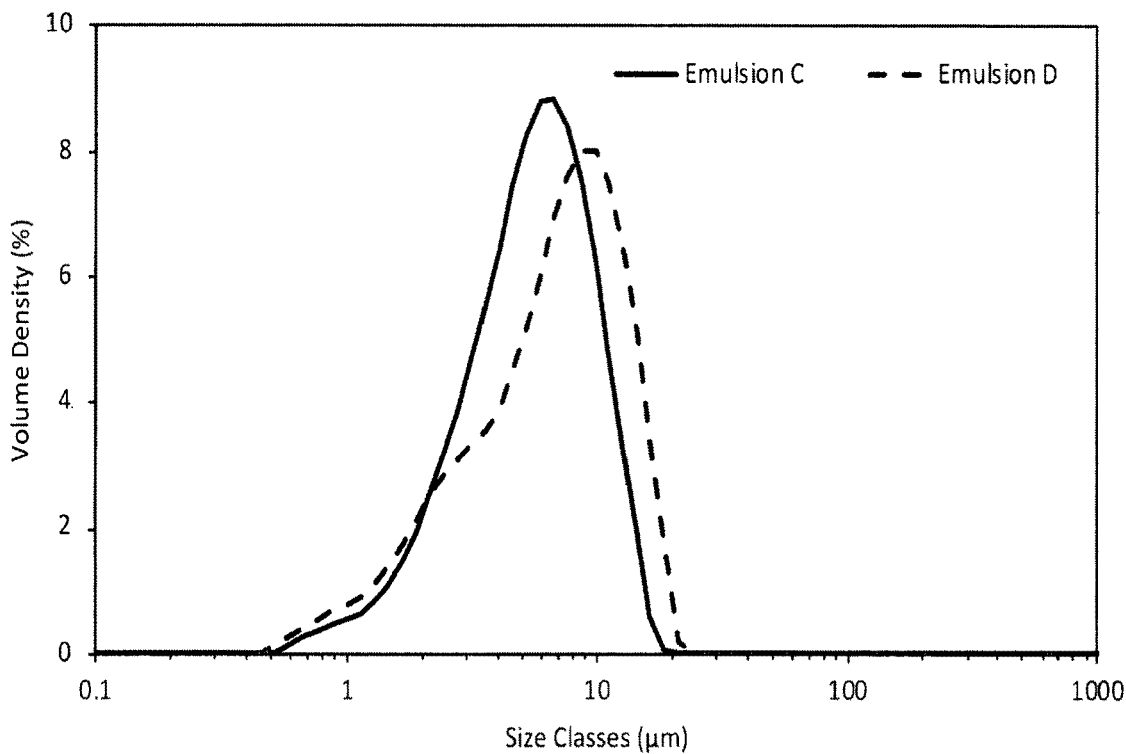
FIG. 3 shows the droplet size volume weighted distribution for emulsions containing the dispersion stabiliser of the invention (Emulsion C) and OSA-starch alone (Emulsion D) within 1 hour of preparation in the presence of xanthan gum.
Figure 4:
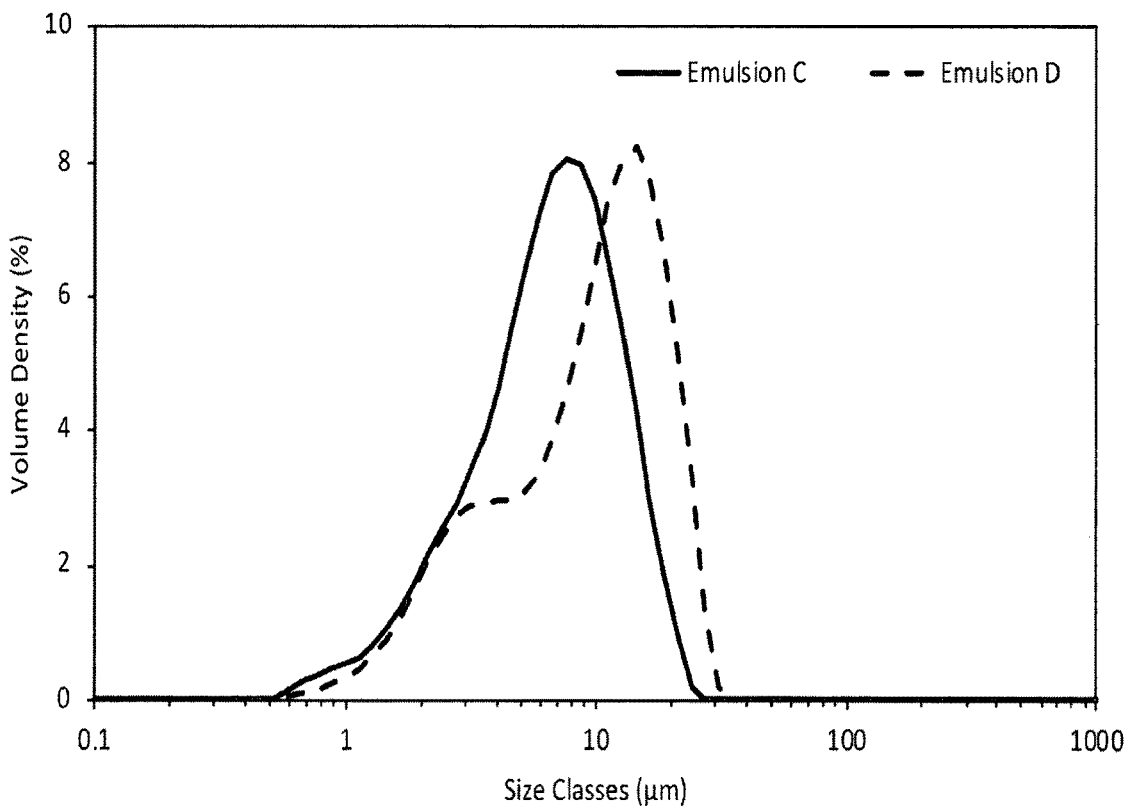
FIG. 4 shows the droplet size volume weighted distribution for an emulsion containing the dispersion stabiliser of the invention (Emulsion C) and by OSA-starch alone (Emulsion D) in the presence of xanthan gum after storage for 5 weeks at 45° C.

The droplet size distribution was measured using a Malvern Mastersizer 3000 as described in Example 1. FIG. 3 illustrates the droplet size distributions of Emulsions C and D within an hour of preparation. The size distributions of both emulsions were similar. The emulsions were then stored at 45° C. and the particle size distributions measured at weekly intervals. FIG. 4 shows the size distributions of both emulsions after five weeks. The droplet size for Emulsion C increased slightly but for Emulsion D the increase in droplet size was more significant. The values for d10, d50 and d90 for each emulsion 1 hour after preparation and after 5 weeks at 45° C. are presented in Table 2. The growth in size with time is clearly seen in the increase in d50 and d90 for Emulsion D in particular. Creaming of the dispersed oil droplets was followed visually. Emulsion C showed no creaming over 5 weeks at 45° C. while Emulsion D showed severe creaming (emulsion phase occupied just 43% of the total volume).

TABLE 2 d10, d50 and d90 droplet size for Emulsions C and D 1 hour after preparation and after 5 weeks at 45° C.

| Sample | | Initial | 5 Weeks |
|---|---|---|---|
| Emulsion C | d10 (μm) | 2.39 | 2.46 |
| | d50 (μm) | 5.94 | 7.15 |
| | d90 (μm) | 11.4 | 14.6 |
| Emulsion D | d10 (μm) | 2.12 | 2.69 |
| | d50 (μm) | 7.37 | 10.8 |
| | d90 (μm) | 14.6 | 21.2 |

This example demonstrates that an emulsion prepared with the dispersion stabiliser of the invention and xanthan has greater stability to coalescence and much more resistance to creaming than a comparative emulsion without CB[n].

EXAMPLE 3

Effect of an Aloe Vera extract on the stability of a sunflower oil oil-in-water emulsion Solutions of 8% w/w OSA-starch and 8.88% w/w dispersion stabiliser were prepared as described in Example 1. A solution of 0.5% w/w xanthan gum was prepared by slowly adding 2.50 g xanthan gum to 497.50 g deionised water whilst stirring on an overhead stirrer at 400 rpm. 0.20 g potassium sorbate was then added to this solution. A 2% w/w solution of aloe vera extract was prepared by mixing 2.00 g Aloe Vera powder (Inovia 90485 SA Cert Organic Aloe Vera 200:1 Powder) with 98.00 g deionised water under stirring.

The aqueous phase of Emulsion E was prepared by combining 7.50 mL of 8.88% w/w dispersion stabiliser with 7.50 mL of 0.5% w/w xanthan gum solution and 7.50 mL 2% w/w Aloe Vera solution and mixing for 5 minutes at 5,000 rpm on a Silverson L5 High Shear Laboratory Mixer with small head (a ⅝" micro general purpose disintegrating head). To this aqueous phase was added 8.57 mL sunflower oil and mixed at 10,000 rpm for 20 minutes to form Emulsion E comprising 2.22% w/w dispersion stabiliser which contains 2.0% w/w OSA-starch.

The aqueous phase of Emulsion F was prepared by combining 7.50 mL of 8% w/w OSA-starch with 7.50 mL of 0.5% w/w xanthan gum solution and 7.50 mL of 2% w/w Aloe Vera solution and mixing for 5 minutes at 5,000 rpm on Silverson L5 High Shear Laboratory Mixer with small head (a ⅝" micro general purpose disintegrating head). To this aqueous phase was added 8.57 mL sunflower oil was added and mixed at 10,000 rpm for 20 minutes to form Emulsion F comprising 2.0% w/w OSA-starch.

Figure 5:
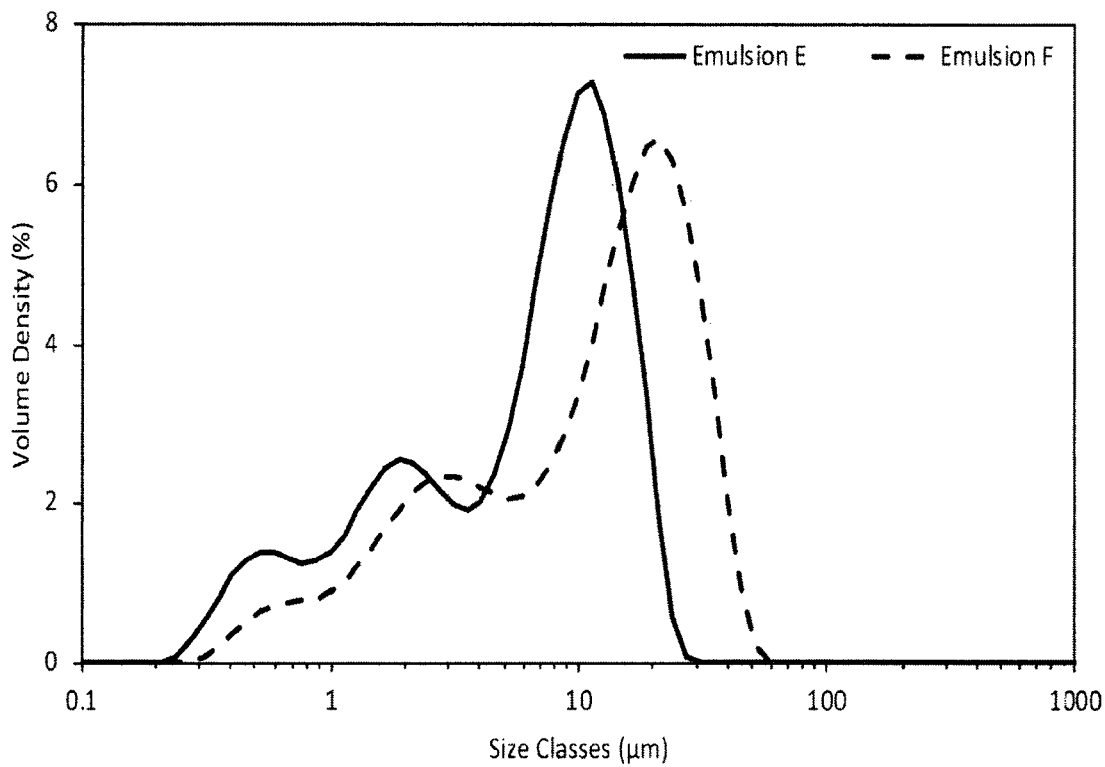
FIG. 5 shows the droplet size volume weighted distribution for emulsions containing the dispersion stabiliser of the invention (Emulsion E) and by OSA-starch alone (Emulsion F) in the presence of xanthan gum and Aloe Vera extract within 1 hour of preparation.

The droplet size distribution was measured using a Malvern Mastersizer 3000 as described in Example 1. FIG. 5 shows the droplet size distributions of the emulsions within one hour of preparation. The size distribution of Emulsion F is significantly larger than Emulsion E as summarised in Table 3Table 3.

TABLE 3 d10, d50 and d90 droplet size for Emulsions E and F 1 hour after preparation

| Sample | | Initial |
| --- | --- | --- |
| Emulsion E | d10 (μm) | 0.92 |
| | d50 (μm) | 7.69 |
| | d90 (μm) | 16.7 |
| Emulsion F | d10 (μm) | 1.72 |
| | d50 (μm) | 13.5 |
| | d90 (μm) | 32.2 |

Creaming of the dispersed oil droplets at 45° C. was observed visually. Emulsion F showed creaming after one day at 45° C. (emulsion phase occupied 43% of the total volume) whilst Emulsion E did not show creaming in that time. After 3 weeks at 45° C., Emulsion E still did not show creaming.

The dispersion stabiliser of the invention stabilises emulsions containing aqueous Aloe Vera more effectively than OS-starch, producing a smaller initial particle size and greater resistance to creaming.

EXAMPLE 4

The Effect of Argan Oil on the Stability of Emulsions Formed with OSA-Starch or the Emulsion Stabiliser of Example 1

Solutions of 8% w/w OSA-starch and 8.88% w/w dispersion stabiliser were prepared as described in Example 1. A solution of 0.5% w/w xanthan gum was prepared as described in Example 3.

The aqueous phase for Emulsion G was prepared by combining 7.50 mL of 8.88% w/w dispersion stabiliser with 7.50 mL of 0.5% w/w xanthan gum solution and 7.50 mL of deionised water and mixing for 5 minutes at 5,000 rpm on a Silverson L5 High Shear Laboratory Mixer with small head (a ⅝" micro general purpose disintegrating head). To this aqueous phase was added 8.57 mL Argan oil and the two phases mixed at 10,000 rpm for 20 minutes to form Emulsion G comprising 2.22% w/w dispersion stabiliser which contains 2.0% w/w OSA-starch.

The aqueous phase of Emulsion H was prepared by combining 7.50 mL of 8% w/w OSA-starch with 7.50 mL of 0.5% w/w xanthan gum solution and 7.50 mL of deionised water and mixing for 5 minutes at 5,000 rpm on a Silverson L5 High Shear Laboratory Mixer with small head (a ⅝" micro general purpose disintegrating head). To this aqueous phase was added 8.57 mL Argan oil and the two phases mixed at 10,000 rpm for 20 minutes to form Emulsion F comprising 2.0% w/w OSA-starch.

Figure 6:
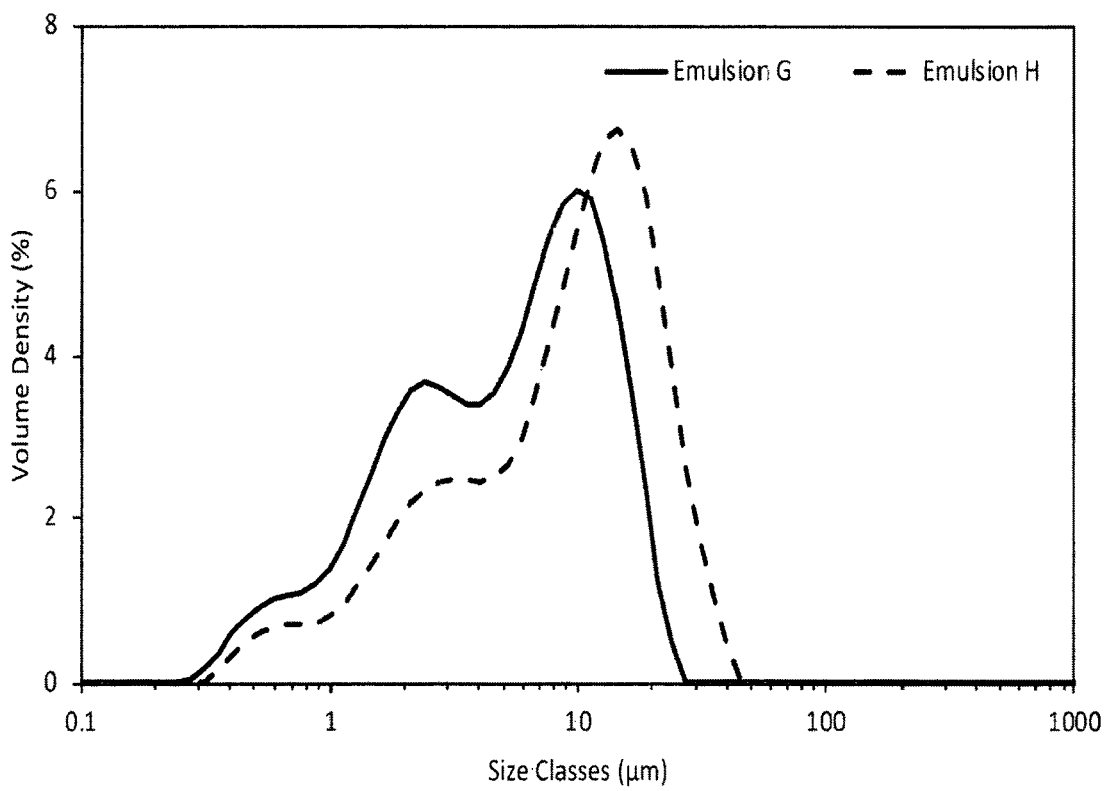
FIG. 6 shows the droplet size volume weighted distribution for Argan oil based emulsions containing the dispersion stabiliser of the invention (Emulsion G) and OSA-starch (Emulsion H) in the presence of xanthan gum within 1 hour of preparation.

The droplet size distribution was measured using a Malvern Mastersizer 3000 as described in Example 1. Table 4 and FIG. 6 show that the droplet size distribution of Emulsion G is less than that for Emulsion H within an hour of preparation. No creaming was seen on preparation of the emulsions.

TABLE 4 d10, d50 and d90 droplet size for Emulsions G and H 1 hour after preparation

| Sample | | Initial |
| --- | --- | --- |
| Emulsion G | d10 (μm) | 1.24 |
| | d50 (μm) | 5.93 |
| | d90 (μm) | 15.4 |
| Emulsion H | d10 (μm) | 1.78 |
| | d50 (pm) | 10.4 |
| | d90 (μm) | 24.0 |

EXAMPLE 5

The Effect of a 40% Oil Blend on the Stability of an Emulsion Formed with the Emulsion Stabiliser of Example 1

It is advantageous to be able to form stable emulsions at high oil content and with blends of oils.

A powder was prepared by weighing 15.00 g of CB[n] and 135.00 g of OSA-starch into a baffled flask and mixing by tumbling the powder for 1 hour. A solution of 8.8% dispersion stabiliser according to the invention was prepared by adding 20.02 g of this mixed powder to 207.48 g of deionised water and leaving to stir overnight. The solution was then placed in a fan-assisted oven at 80° C. for 2 hours thereby to produce an 8.8% w/w solution of dispersion stabiliser. A 0.5% w/w solution of xanthan gum was prepared by slowly adding 1.00 g of xanthan gum and 0.10 g of potassium sorbate to 198.91 g of deionised water.

The aqueous phase of Emulsion I was prepared by combining 4.09 mL of the 8.8% w/w dispersion stabiliser with 4.50 mL of 0.5% w/w xanthan gum and 9.41 mL of deionised water and mixing for 5 minutes at 5,000 rpm on a Silverson L5 High Shear Laboratory Mixer with small head(a ⅝" micro general purpose disintegrating head). To this aqueous phase was added 13.03 mL of an oil solution rich in safflower oil and mixed at 10,000 rpm for 20 minutes to form Emulsion I comprising 2.0% w/w dispersion stabiliser. The oil solution contained primarily refined organic safflower oil and also organic Jojoba oil, fragrance and tocopherol.

Figure 7:
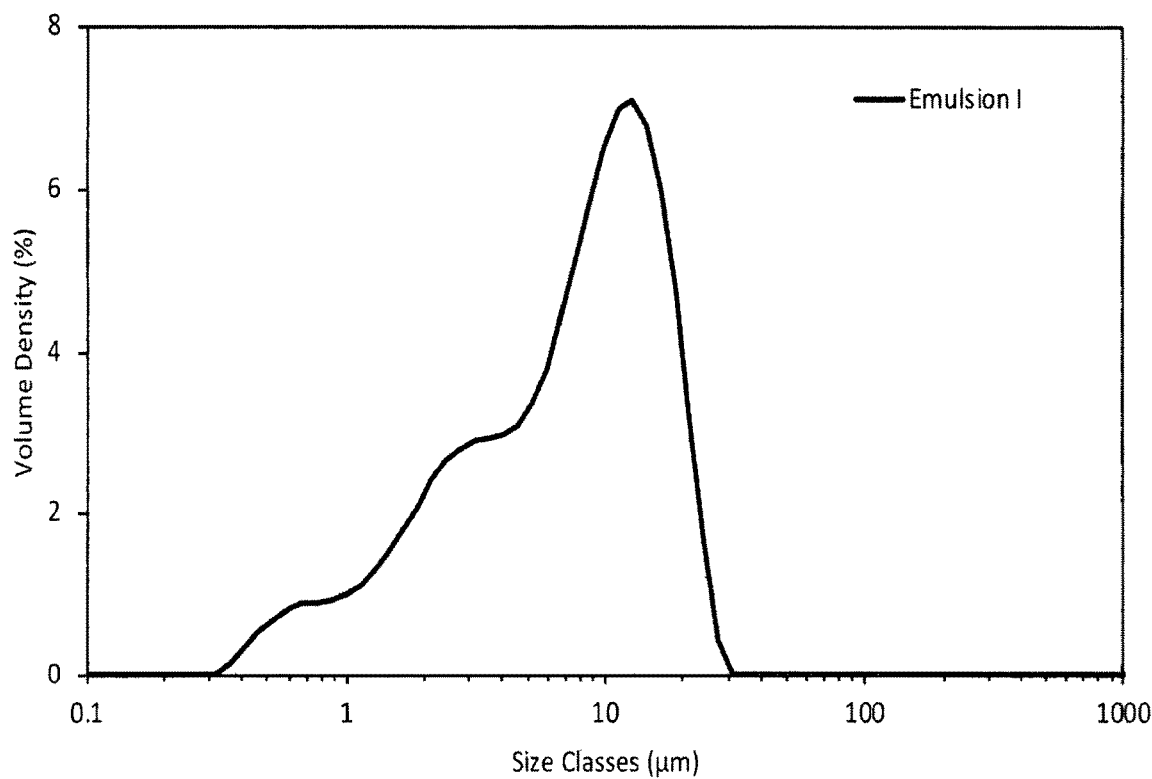
FIG. 7 shows the droplet size volume weighted distribution for an oil blend based emulsion containing the dispersion stabiliser of the invention in the presence of xanthan gum within 1 hour of preparation.
Figure 8:
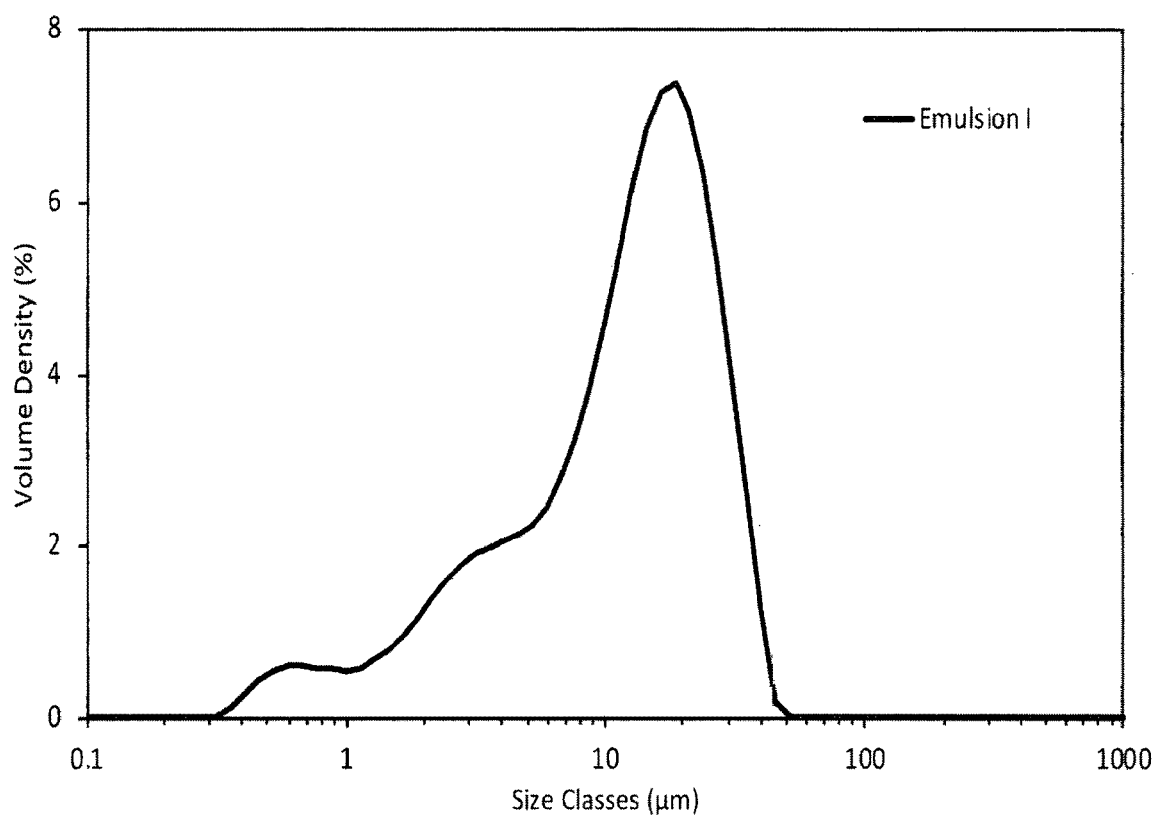
FIG. 8 shows the droplet size volume weighted distribution for an oil blend based emulsion containing the dispersion stabiliser of the invention in the presence of xanthan gum after storage for 8 weeks at 45° C.

The droplet size distribution was measured using a Malvern Mastersizer 3000. The distributions are of two samplings, each of which was measured 5 times (sub runs), corresponding to 10 individual measurements. FIG. 7 shows the droplet size distribution of Emulsion I within an hour of preparation and FIG. 8 shows the droplet size distribution of Emulsion I after 8 weeks storage at 45° C. The corresponding values for d10, d50 and d90 are presented in Table 5.

TABLE 5 d10, d50 and d90 droplet size for Emulsion I 1 hour after preparation and after 8 weeks storage at 45° C.

| Sample | | Initial | 8 Weeks |
|---|---|---|---|
| Emulsion I | d10 (μm) | 1.62 | 2.45 |
| | d50 (μm) | 8.55 | 13.9 |
| | d90 (μm) | 18.7 | 29.5 |

Creaming of the dispersed oil droplets was followed visually. Emulsion I showed very little creaming (emulsion phase occupied 80% of the total volume)) after 8 weeks storage at 45° C. Thus the dispersion stabiliser of the invention was able to emulsify an oil blend, primarily consisting of safflower oil, at 40% w/w.

EXAMPLE 6

Emulsions Formed with the Dispersion Stabiliser of the Invention Dispersed in the Aqueous or the Oil Phase It is advantageous to be able to prepare emulsions with an emulsifier dispersed in either the aqueous and/or the oil phases. Dispersion followed immediately by emulsification is advantageous in eliminating any starch dissolution step.

The dispersion stabiliser powder and 0.5% w/w aqueous solution of xanthan gum of Example 5 were prepared. A solution of 0.02% Oil Red O in caprylyl methicone was prepared as described in Example 1.

The aqueous phase of Emulsion J was prepared by adding 0.456 g dispersion stabiliser powder to 5.70 mL of 0.5% w/w xanthan gum solution and 17.10 mL of 0.05% w/w potassium sorbate solution. This aqueous phase was premixed at 5,000 rpm on a Silverson L5 High Shear Laboratory Mixer with a small head (a ⅝" micro general purpose disintegrating head) for 5 minutes. 8.65 mL of 0.02% w/w Oil Red O in caprylyl methicone solution was then added over 30 seconds before mixing for 20 minutes at 10,000 rpm.

The aqueous phase of Emulsion K was prepared by adding 5.70 mL of 0.5% w/w xanthan gum solution to 17.10 mL of 0.05% w/w potassium sorbate solution and premixing at 5,000 rpm on a Silverson L5 High Shear Laboratory Mixer with a small head (a ⅝" micro general purpose disintegrating head) for 5 minutes. 0.456 g dispersion stabiliser powder was dispersed in 8.65 mL of 0.02% w/w Oil Red O in caprylyl methicone solution before the aqueous phase was added to the oil phase. The two phases were then mixed for 20 minutes at 10,000 rpm.

Figure 9:
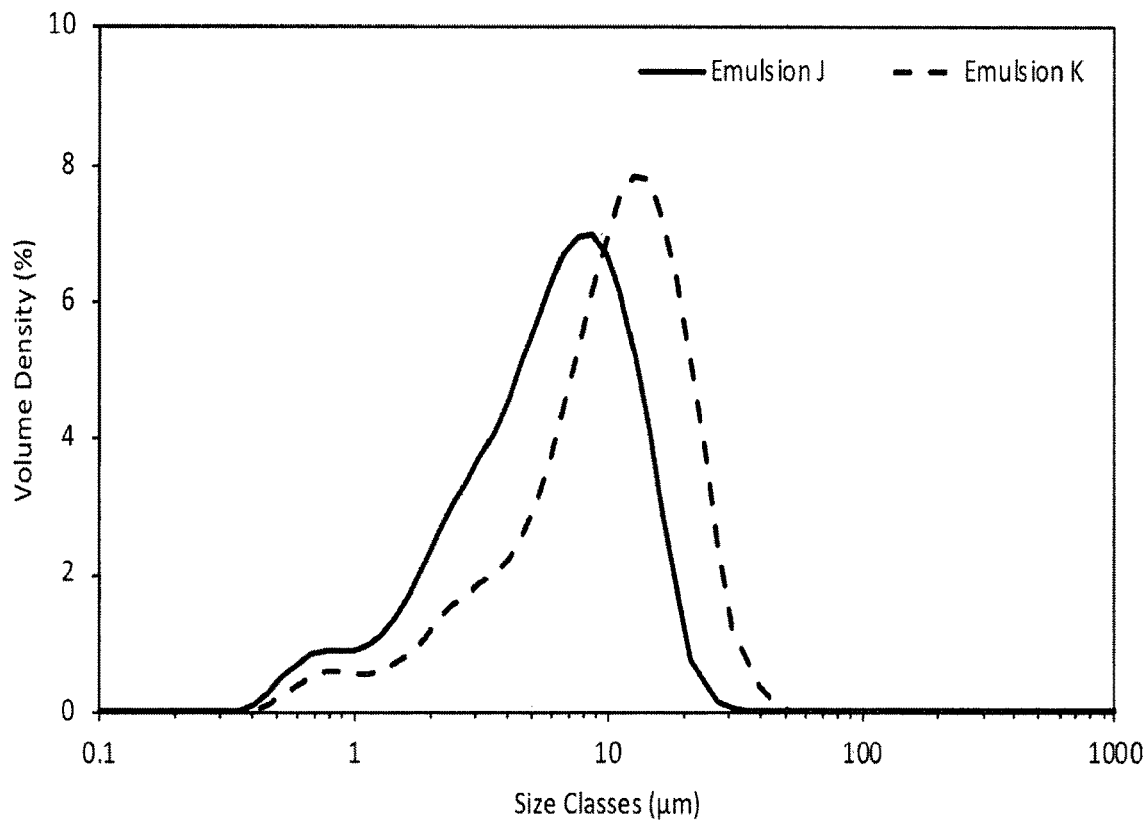
FIG. 9 shows the droplet size volume weighted distribution for emulsions containing the dispersion stabiliser of the invention introduced into the aqueous phase (Emulsion J) or oil phase (Emulsion K) in the presence of xanthan gum within 1 hour of preparation.
Figure 10:
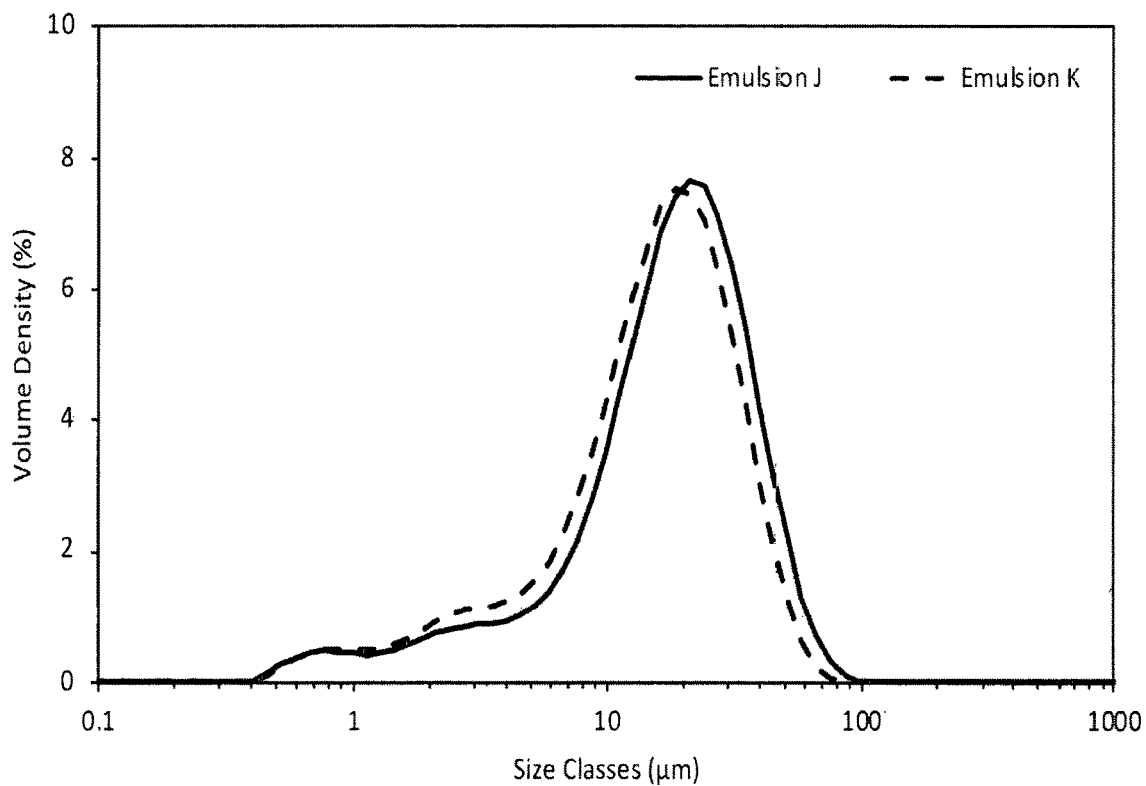
FIG. 10 shows the droplet size volume weighted distribution for emulsions containing the dispersion stabiliser of the invention introduced into the aqueous phase (Emulsion J) or oil phase (Emulsion K) in the presence of xanthan gum after storage for 4 weeks at 45° C.

The droplet size distribution was measured using a Malvern Mastersizer 3000 as described in Example 5. FIG. 9 shows the droplet size distribution of Emulsions J and K within an hour of preparation and FIG. 10, the droplet size distribution of Emulsions J and K after 4 weeks storage at 45° C. The corresponding values for d10, d50 and d90 are presented in Table 6Table 6.

TABLE 6 d10, d50 and d90 droplet size for Emulsions J and K 1 hour after preparation and after 4 weeks storage at 45° C.

| Sample | | Initial | 4 Weeks |
|---|---|---|---|
| Emulsion J | d10 (μm) | 1.82 | 4.29 |
| | d50 (μm) | 6.61 | 19.8 |
| | d90 (μm) | 14.7 | 42.5 |
| Emulsion K | d10 (μm) | 2.84 | 3.54 |
| | d50 (μm) | 11.3 | 17.1 |
| | d90 (μm) | 23.4 | 36.9 |

Creaming of the dispersed oil droplets was followed visually. Creaming was only observed after 4 weeks storage at 45° C. However Emulsion J showed significantly less creaming (emulsion phase occupied 75% of total volume) than Emulsion K (emulsion phase occupied 51% of total volume). Emulsions were successfully prepared by dispersing dispersion stabiliser powder in either the oil phase or aqueous phase through cold processing.

EXAMPLE 7

Emulsions Formed with Sorbitan Monolaurate (SPAN-20) in the Oil Phase and the Dispersion Stabiliser of the Invention Dispersed in Either the Aqueous or Oil Phase It is advantageous to be able to form emulsions with non-ionic surfactant in the oil phase by dispersing the dispersion stabiliser in either the oil or aqueous phases. Dispersion followed immediately by emulsification is advantageous in eliminating any starch dissolution step.

An oil solution of 1% w/w SPAN-20 (HLB 8.6) in caprylyl methicone was prepared by adding 0.52 g of SPAN-20 to 49.50 g of 0.02% w/w Oil Red O in caprylyl methicone. Dispersion stabiliser powder and a 0.5% w/w xanthan gum solution were prepared as described in Example 5.

The aqueous phase for Emulsion L was prepared by adding 0.456 g dispersion stabiliser powder to 5.70 mL of 0.5% w/w xanthan gum solution and 17.10 mL of 0.05% w/w potassium sorbate solution. This aqueous phase was premixed at 5,000 rpm on a Silverson L5 High Speed Laboratory Mixer with a small head (a ⅝" micro general purpose disintegrating head) for 5 minutes. 8.65 mL of the oil phase was then added over 30 seconds before mixing for 20 minutes at 10,000 rpm.

The aqueous phase for Emulsion M was prepared by adding 5.70 mL of 0.5% w/w xanthan gum solution to 17.10 mL of 0.05% w/w potassium sorbate solution and premixing at 5,000 rpm on a Silverson L5 High Shear Laboratory Mixer with a small head (a ⅝" micro general purpose disintegrating head) for 5 minutes. 0.456 g dispersion stabiliser powder was dispersed in 8.65 mL of the oil phase before the aqueous phase was added to the oil phase. The two phases were then mixed for 20 minutes at 10,000 rpm.

Figure 11:
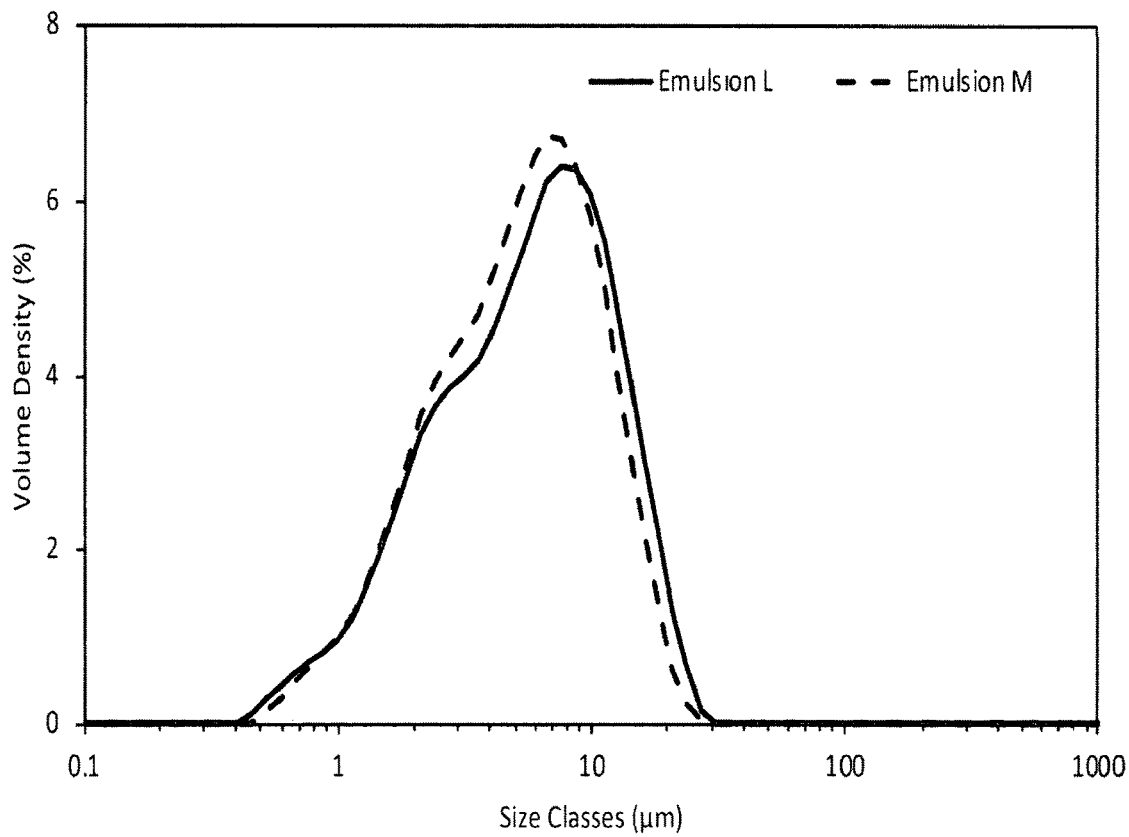
FIG. 11 shows the droplet size volume weighted distribution for emulsions containing the dispersion stabiliser of the invention introduced into the aqueous phase (Emulsion L) or oil phase (Emulsion M) in the presence of xanthan gum and sorbitan monolaurate (Span 20) within 1 hour of preparation.
Figure 12:
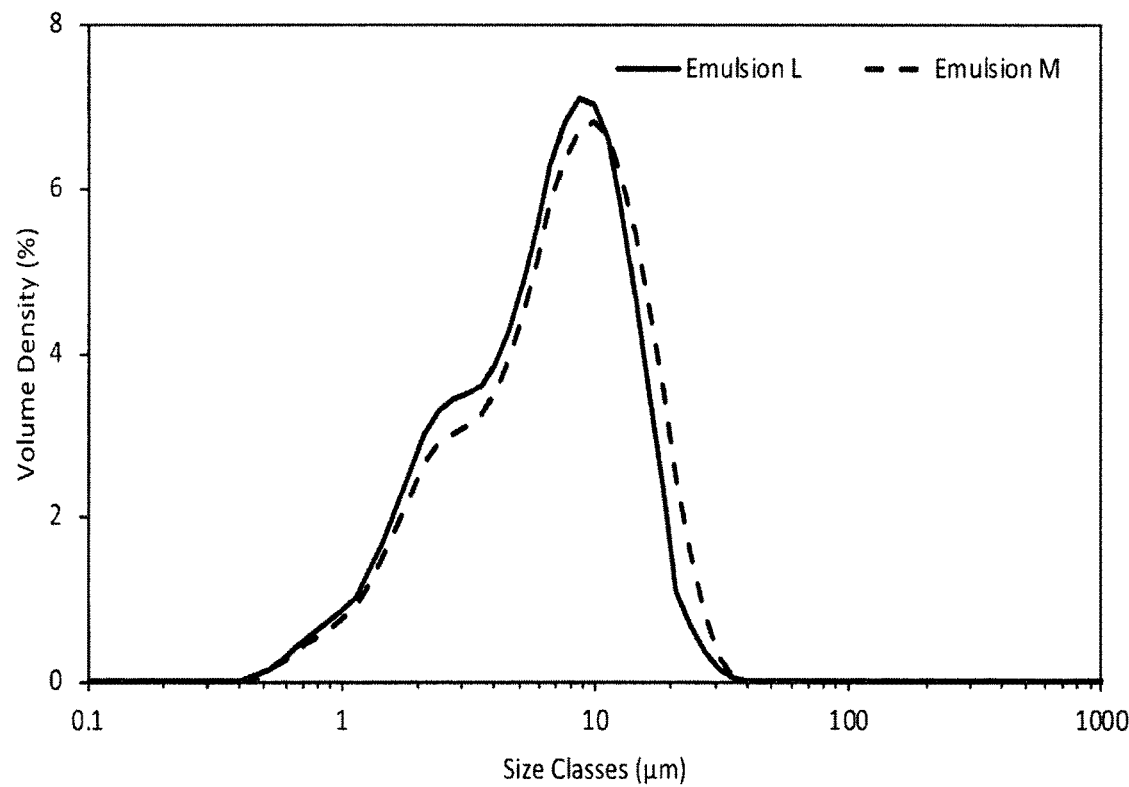
FIG. 12 shows the droplet size volume weighted distribution for emulsions containing the dispersion stabiliser of the invention introduced into the aqueous phase (Emulsion L) or oil phase (Emulsion M) in the presence of xanthan gum and sorbitan monolaurate (Span 20) after storage for 2 weeks at 45° C.

The droplet size distribution was measured using a Malvern Mastersizer 3000 as described in Example 5. FIG. 11 shows the droplet size distribution of Emulsions L and M within an hour of preparation and FIG. 12, the droplet size distribution of Emulsions L and M after 2 weeks storage at 45° C. The corresponding values for d10, d50 and d90 are presented in Table 7Table 7.

TABLE 7 d10, d50 and d90 droplet size for Emulsions L and M 1 hour after preparation and after 2 weeks storage at 45° C.

| Sample | | Initial | 2 Weeks |
|---|---|---|---|
| Emulsion L | d10 (µm) | 1.77 | 1.93 |
| | d50 (µm) | 6.22 | 7.06 |
| | d90 (µm) | 14.9 | 15.6 |
| Emulsion M | d10 (µm) | 1.80 | 2.06 |
| | d50 (µm) | 5.74 | 7.87 |
| | d90 (µm) | 13.3 | 18.0 |

Creaming of the dispersed oil droplets was followed visually. Some creaming was only observed after 2 weeks storage at 45° C. However Emulsion L showed slightly less creaming (emulsion phase occupied 92% of the total volume) than Emulsion M (emulsion phase occupied 81% of the total volume).

Incorporation of Span-20 into the oil phase produces stable emulsions with the dispersion stabiliser of the invention dispersed in either the aqueous or oil phases.

EXAMPLE 8

Emulsions Formed at Room Temperature and 80° C. with the Dispersion Stabiliser of the Invention Dispersed in Castor Oil It is advantageous to be able to form emulsions by dispersing the dispersion stabiliser of the invention in the oil phase at room temperature or 80° C.

The dispersion stabiliser powder and 0.5% w/w xanthan gum solution of Example 5 were prepared.

The aqueous phase of Emulsion N was prepared by combining 5.70 mL of 0.5% w/w xanthan gum solution and 17.10 mL of 0.5% w/w potassium sorbate solution which was then premixed at 5,000 rpm on a Silverson L5 High Shear Laboratory Mixer with a small head (a ⅝" micro general purpose disintegrating head) for 5 minutes. 0.60 g dispersion stabiliser powder was dispersed in 7.50 mL castor oil using a magnetic stirrer. The aqueous phase was then added to the oil phase and mixed for 20 minutes at 10,000 rpm.

The aqueous phase of Emulsion O was prepared by combining 5.70 mL of 0.5% w/w xanthan gum solution and 17.10 mL of 0.5% w/w potassium sorbate solution and premixing them at 5000 rpm on a Silverson L5 High Shear Laboratory Mixer (a ⅝" micro general purpose disintegrating head) with a small head for 5 minutes before heating on a stirrer plate to 80° C. 0.60 g dispersion stabiliser powder was dispersed in 7.50 mL castor oil using a magnetic stirrer and heated to 80° C. on a stirrer hotplate. The aqueous phase was heated to 80° C. then added to the oil phase and mixed for 20 minutes at 10,000 rpm.

Figure 13:
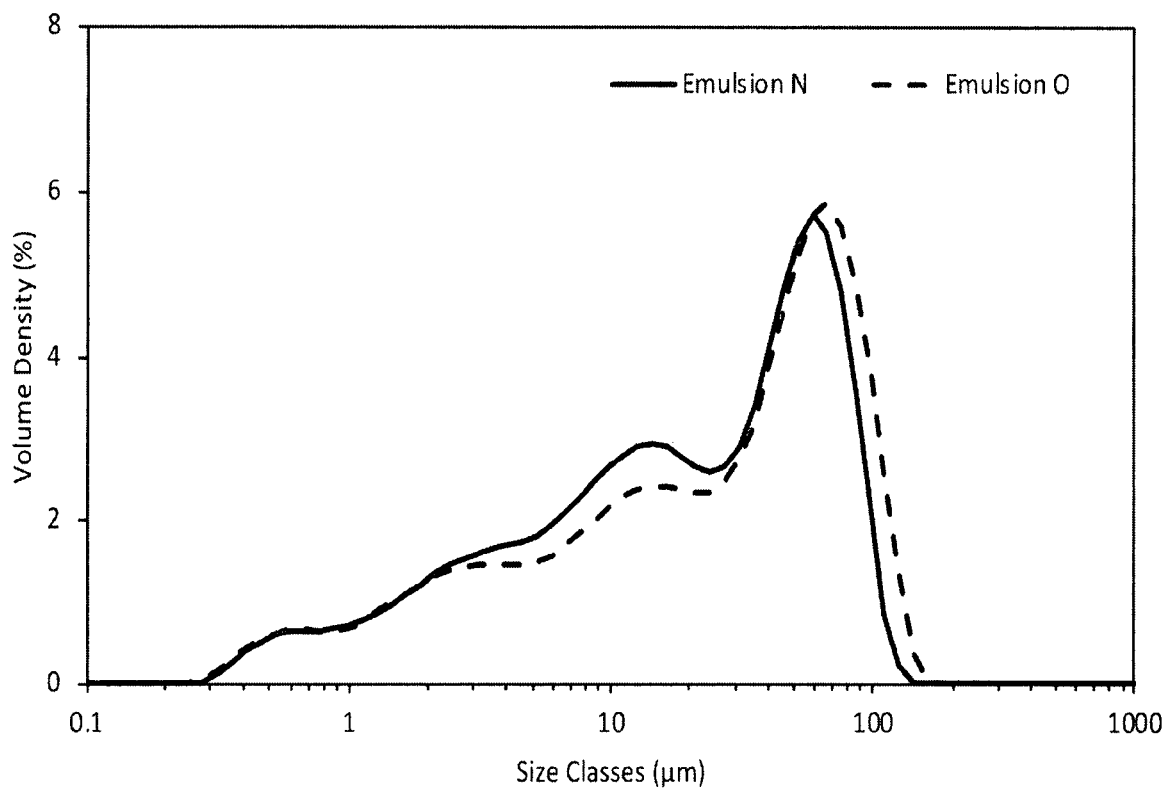
FIG. 13 shows the droplet size volume weighted distribution for emulsions containing the dispersion stabiliser of the invention introduced into the oil phase wherein emulsions were formed at room temperature (Emulsion N) or 80° C. (Emulsion O) in the presence of xanthan gum within 1 hour of preparation.
Figure 14:
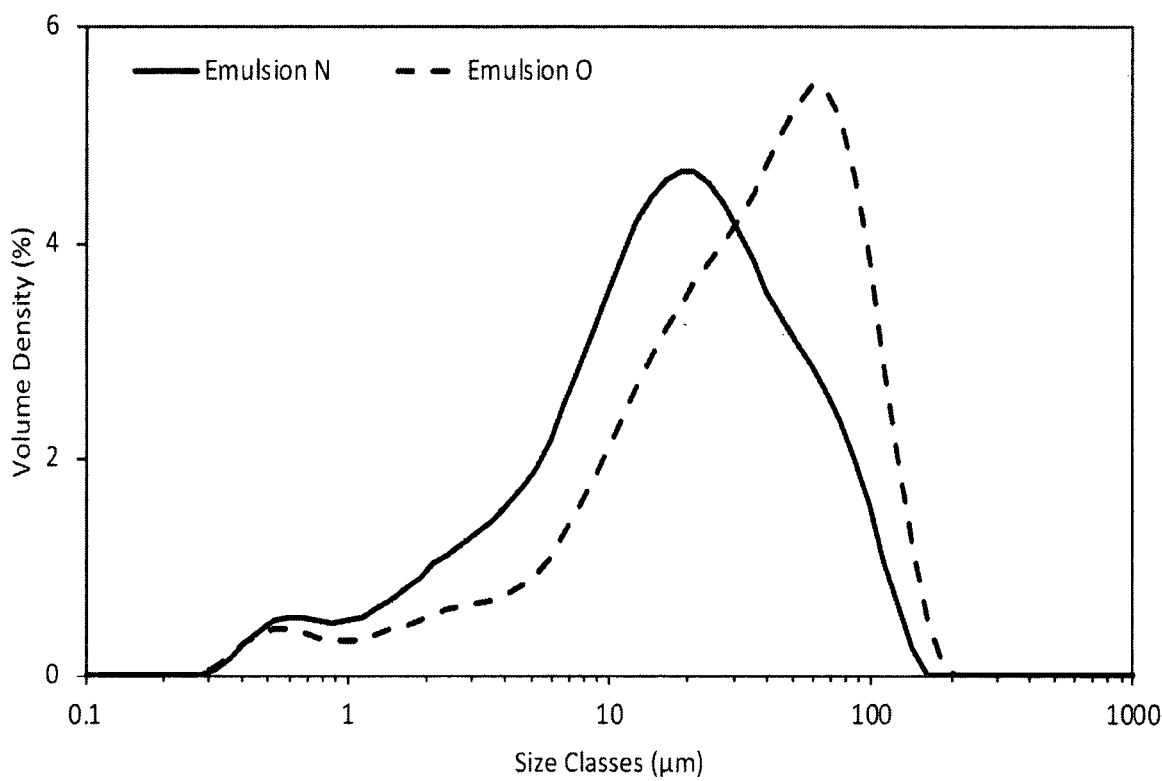
FIG. 14 shows the droplet size volume weighted distribution for emulsions containing the dispersion stabiliser of the invention introduced into the oil phase wherein emulsions were formed at room temperature (Emulsion N) or 80° C. (Emulsion O) in the presence of xanthan gum after storage for 2 weeks at 45° C.

The droplet size distribution was measured using a Malvern Mastersizer 3000 as described in Example 5 and the results for the two emulsions after preparation and after four weeks at 45° C. are presented in FIG. 13, FIG. 14 and in Table 8Table 8.

TABLE 8 d10, d50 and d90 droplet size for Emulsions N and O 1 hour after preparation and after 4 weeks storage at 45° C.

| Sample | | Initial | 4 Weeks |
|---|---|---|---|
| Emulsion N | d10 (µm) | 2.10 | 2.82 |
| | d50 (µm) | 22.5 | 18.5 |
| | d90 (µm) | 79.0 | 68.9 |
| Emulsion O | d10 (µm) | 2.04 | 5.08 |
| | d50 (µm) | 30.5 | 36.1 |
| | d90 (µm) | 93.3 | 100 |

Creaming of the dispersed oil droplets was followed visually. Some creaming was only observed after 4 weeks storage at 45° C. Both Emulsions exhibited approximately the same degree of creaming (emulsion phase occupied approximately 50% of the total volume).

Emulsions can be formed by addition of the dispersion stabiliser of the invention to the oil phase at room temperature and at 80° C.

EXAMPLE 9

Effect of CB[n] on Rheology of Starch Solution

OSA-starch was dissolved in water with stirring overnight at 20° C. Dissolution was speeded by heating the solution, for example, to 70° C. for an hour. Solutions of the dispersion stabiliser were prepared by dry mixing OSA-starch and CB[n] before dissolution or adding CB[n] to a OSA-starch solution. The resulting solutions were identical irrespective of the order of addition.

All rheological measurements were made with a Malvern Kinexus Pro+Rheometer with a 4° 40 mm diameter cone-plate stainless steel geometry with lightly roughened surfaces. The measurement temperature was 20° C. and samples were loaded with a Pasteur pipette before the cone was lowered to the correct position. The sample was pre-sheared to a stress corresponding to a shear rate of 100-300 s$^{-1}$—to ensure homogeneity. The experimental procedure then typically involved a 5-minute period at rest before starting the measurements.

(a) Yield Stress for 2% w/w Dispersion Stabiliser of the Invention by Step Changes in Shear Stress Samples of 2.0% w/w OSA-starch and 2.0% w/w dispersion stabiliser (9:1 OSA-starch:CB[n]) in 0.05% w/w potassium sorbate were prepared as described in Example 1.

Figure 15:
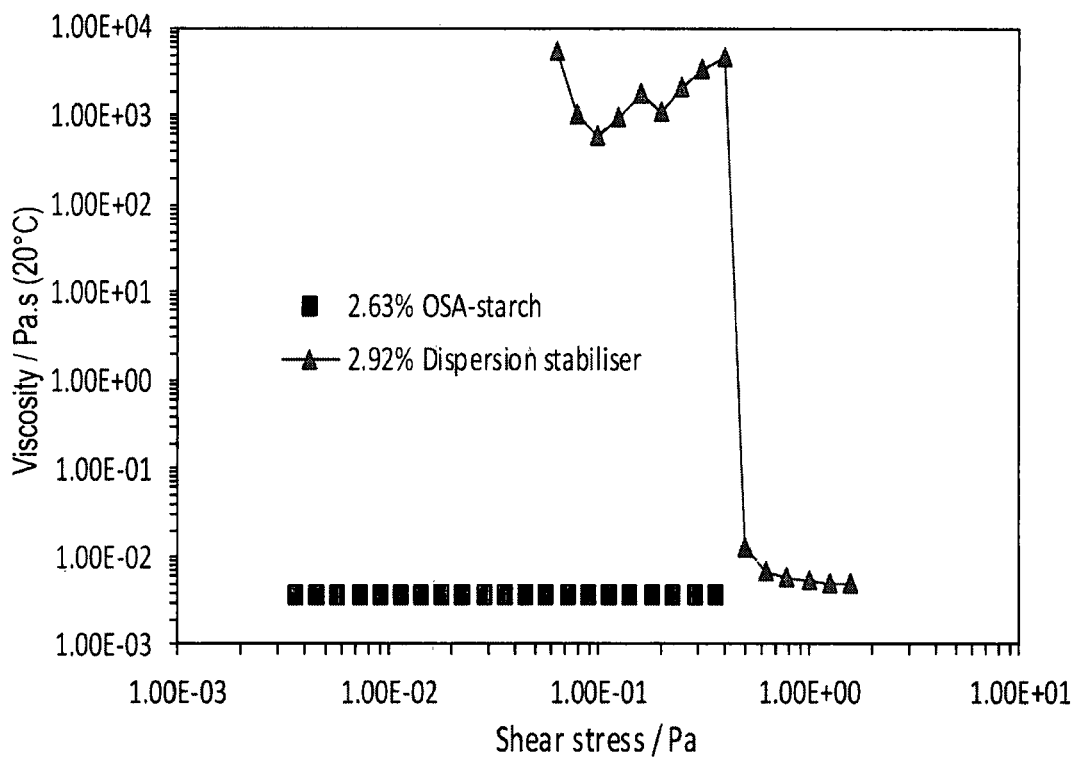
FIG. 15 shows the viscosity as a function of increasing shear stress of 2.0% w/w OSA-starch (squares) and 2.0% w/w dispersion stabiliser of the invention (triangles)
Figure 16:
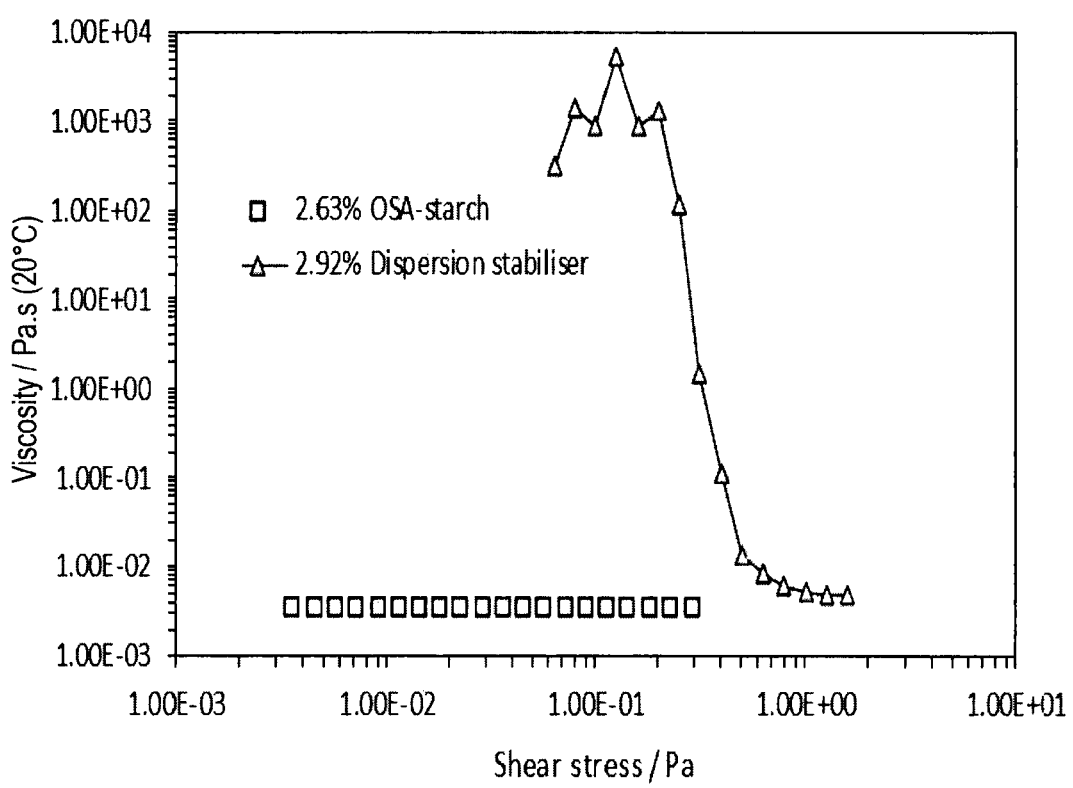
FIG. 16 shows the viscosity as a function of decreasing shear stress of 2.0% w/w OSA-starch (squares) and 2.0% w/w dispersion stabiliser of the invention (triangles)

The viscosity was measured stepwise as a function of increasing (see FIG. 15) and then decreasing (see FIG. 16) shear stress. The 2.0% w/w OSA-starch solution (plotted as squares) was Newtonian (viscosity 2.2 mPa—s and independent of shear). In contrast the 2.0% w/w dispersion stabiliser (9:1 OSA-starch:CB[n], data plotted as triangles and connected by a line) indicated a very high and variable apparent viscosity at low shear. This behaviour is consistent with no or negligible flow (apparent shear rate between $8 \times 10^{-6}$ and $2 \times 10^{-4}$ s$^{-1}$) up to at least 0.4 Pa, followed by a dramatic increase in flow at 0.5 Pa (shear rate 110 s$^{-1}$). On decreasing stress, the viscosity increases gradually from 0.4 Pa, before an arrest in flow below 0.2 Pa. The sharp transitions are consistent with an apparent yield stress and the presence of a weak network structure formed, which is not present in 2.0% w/w OSA-starch solution, thereby demonstrating an interaction between the CB[n] and the OSA-modified starch. The viscosity at stress above 0.4 Pa is similar for the OSA-starch and dispersion stabiliser solutions.

Figure 17:
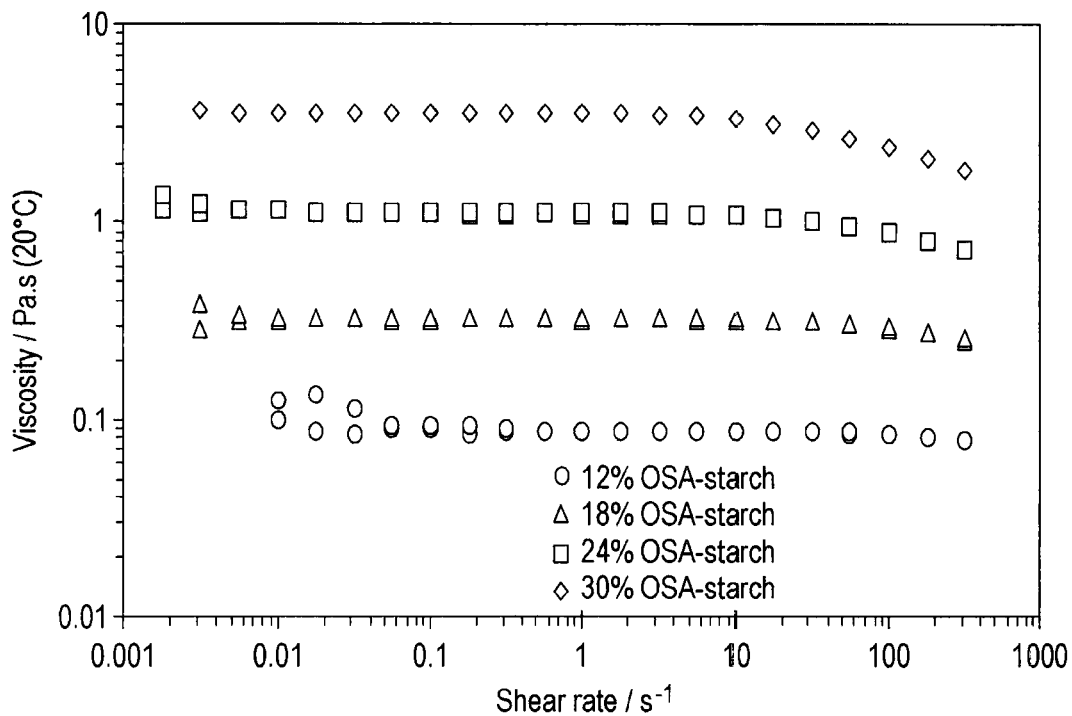
FIG. 17 shows the viscosity of OSA-starch solutions on decreasing then increasing shear rate.

(b) Yield Stress for Dispersion Stabiliser of the Invention Over Wide Range of Concentrations A series of OSA-starch solutions between 12 and 30% w/w in 0.05% w/w aqueous potassium sorbate were prepared in accordance with Example 1. The viscosity was measured stepwise on decreasing then increasing shear rate and the results are shown in FIG. 17. The viscosity increases with concentration of OSA-starch. The solutions are Newtonian to a shear stress (product of viscosity and shear rate) to approximately 10 Pa and are noticeably shear thinning from 100 Pa.

Figure 18:
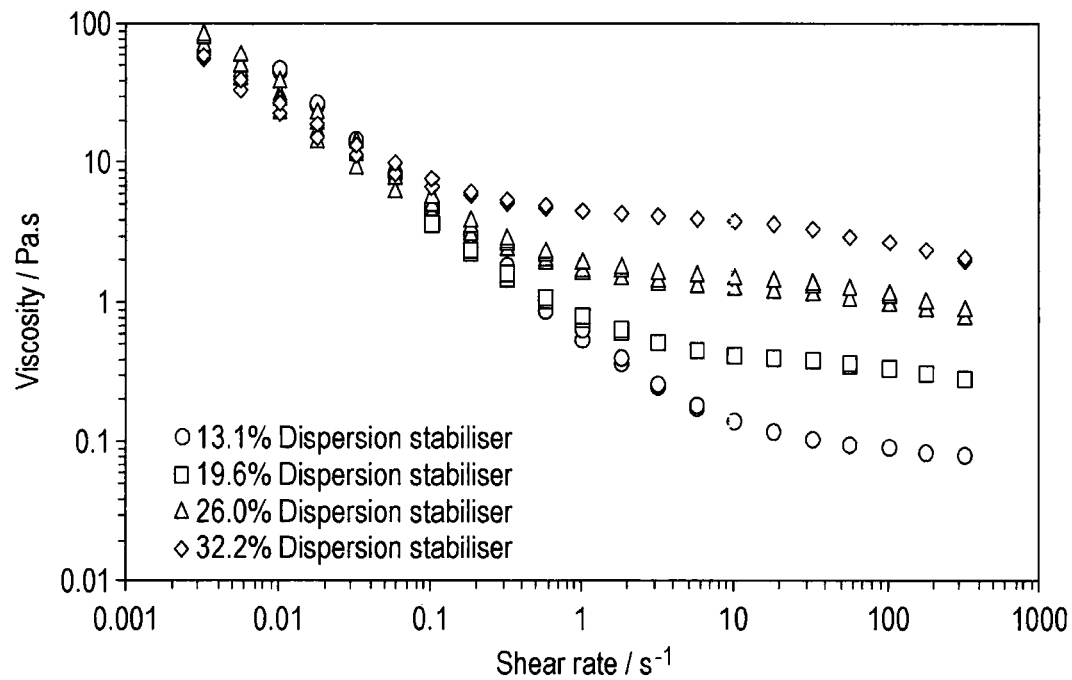
FIG. 18 shows the viscosity of solutions of the dispersion stabiliser of the invention on decreasing then increasing shear rate.

To these OS-starch solutions, CB[n] was added to a concentration of ⅑ of the OSA-starch concentration to form dispersion stabiliser solutions of different concentrations. The samples were stirred with a magnetic follower at room temperature until the appearance was uniform (a period from 16 hours to 3 days was allowed, with time increasing with sample viscosity). The shear sweeps in decreasing then increasing rate were repeated and the results are presented in FIG. 18. At high shear, the OSA-starch and dispersion stabiliser solutions show similar behaviour. However, there is a significant difference in the shear dependence of the viscosity at low rate between the OSA-starch and dispersion stabiliser. For the dispersion stabiliser, instead of Newtonian behaviour below 10 Pa, there is a continuously increasing viscosity below approximately 1 Pa, consistent with an apparent yield stress. The effect of CB[n] on solutions of OS-starch occurs over a very wide range of concentration. In contrast to WO 2013/124654 (Cambridge Enterprise Limited), the viscosity is less than 60 Pa·s at shear rates 0.1-0.5 $s^{-1}$.

Figure 19:
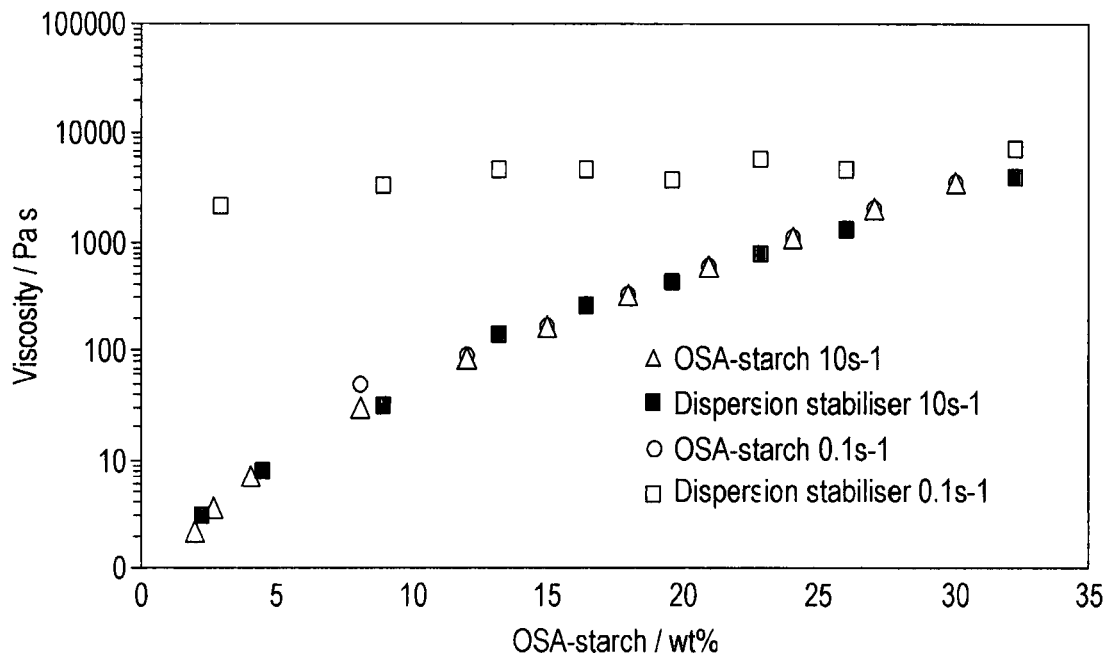
FIG. 19 shows the viscosity at $0.1\ s^{-1}$ and $10\ s^{-1}$ as a function of concentration for OSA-starch and the dispersion stabiliser of the invention.

The effect of CB[n] on the flow behaviour of OSA-starch solutions at high shear can be shown by comparing the viscosity at 10 $s^{-1}$ as a function of OSA-starch concentration for the dispersion stabiliser and for OSA-starch (see FIG. 19). The effect of CB[n] is to increase viscosity slightly. This lack of effect of CB[n] on OSA-starch rheological behaviour at high shear indicates that the presence of CB[n] will not impact significantly the processability of materials containing the dispersion stabiliser.

(c) Effect of Combining the Dispersion Stabiliser of the Invention with Xanthan Gum in Solution Solutions of xanthan at 0.16% w/w, OSA-starch at 2.63% w/w, dispersion stabiliser at 2.92% w/w and combinations thereof were prepared in the manner described in Examples 1 and 2. Rheological studies were made at 20° C.: again, samples were pre-sheared to a stress corresponding to a shear rate of 100-300 $s^{-1}$—to ensure homogeneity. The experimental procedure then typically involved a 5-minute period at rest before starting the measurements.

Figure 20:
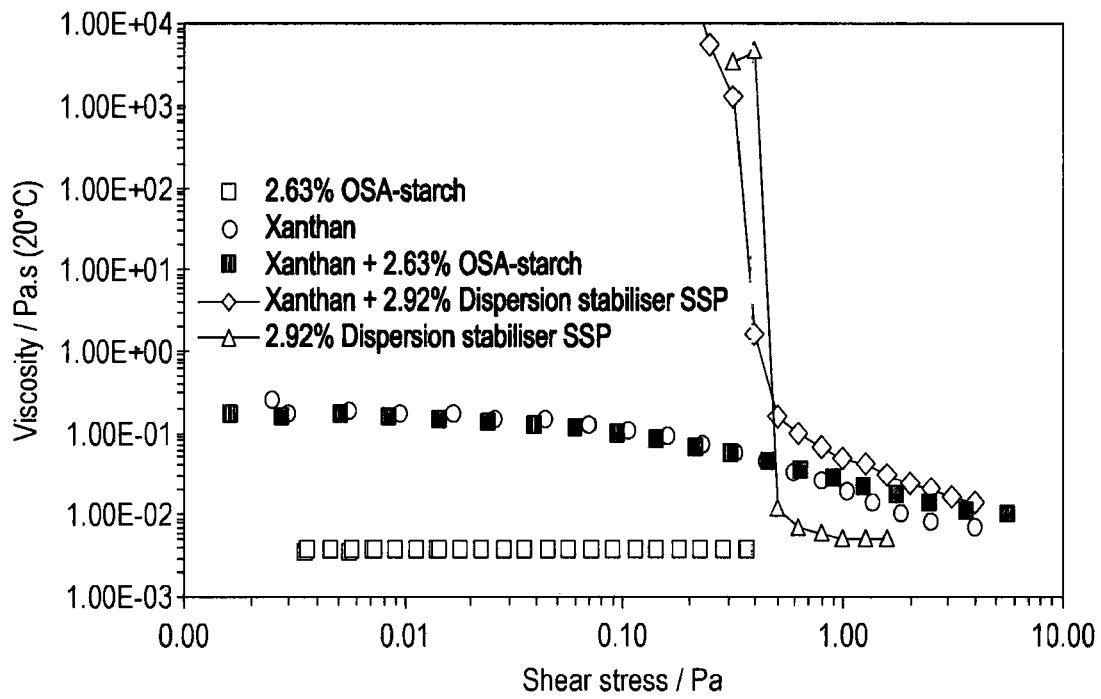
FIG. 20 shows the viscosity as a function of increasing shear stress of solutions containing combinations of xanthan (0.16% w/w), OSA-starch (2.63% w/w), and CB[n] (0.29% w/w)
Figure 21:
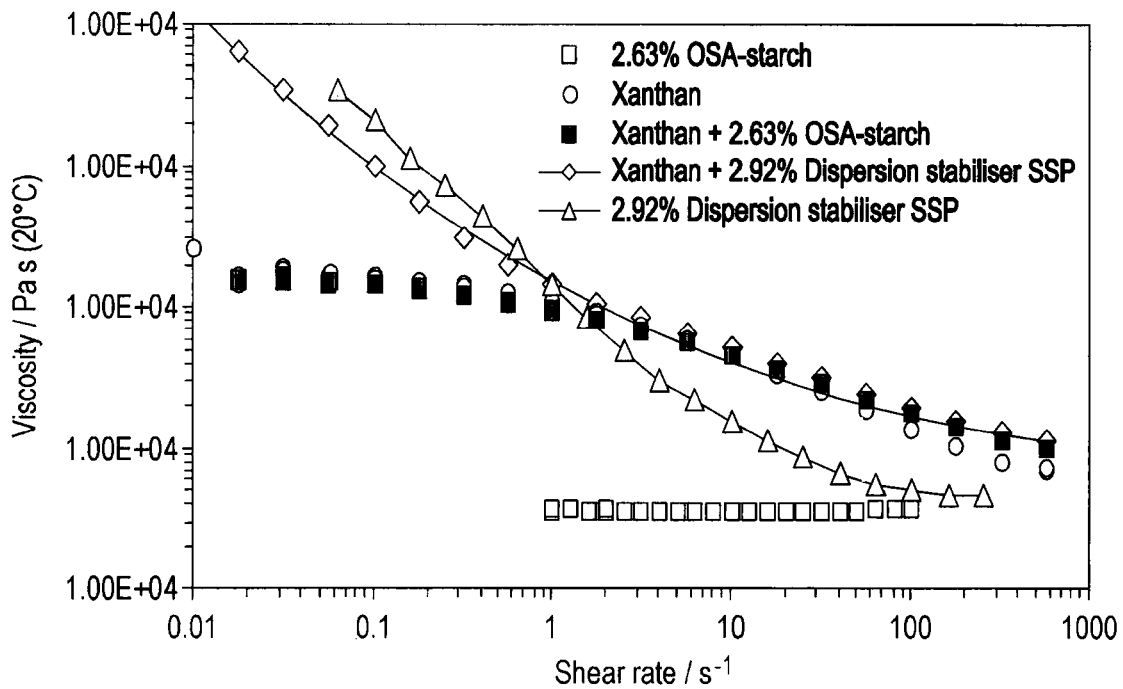
FIG. 21 shows the viscosity as a function of shear rate of solutions containing combinations of xanthan (0.16% w/w), OSA-starch (2.63% w/w), and CB[n] (0.29% w/w)

The rheology of the samples was studied at 20° C. The viscosity of these solutions on stepwise increase in shear is presented in FIG. 20. The 2.63% w/w OSA-starch solution has low viscosity (3.6 mPa·s) and is Newtonian. Solutions of xanthan with OSA-starch or CB[n] showed similar Newtonian behaviour with viscosities of about 250 mPa·s at low shear stress and weak shear thinning behaviour above 0.01 Pa. Solutions in which both OSA-starch and CB[n] are present, however, show rheological behaviour consistent with a yield stress: both with and without xanthan, the apparent sample viscosity is very high up to 0.4 Pa (with no significant flow detectable), whilst above 0.4 Pa, the viscosity falls sharply and the limiting high-shear viscosity is close to the corresponding sample composition without CB[n]. FIG. 21 shows the viscosity as a function of shear rate of solutions containing combinations of xanthan (0.16% w/w), OSA-starch (2.63% w/w), and CB[n] (0.29% w/w). The viscosity is less than 60 Pa·s at shear rates 0.1-0.5 $s^{-1}$.

Figure 22:
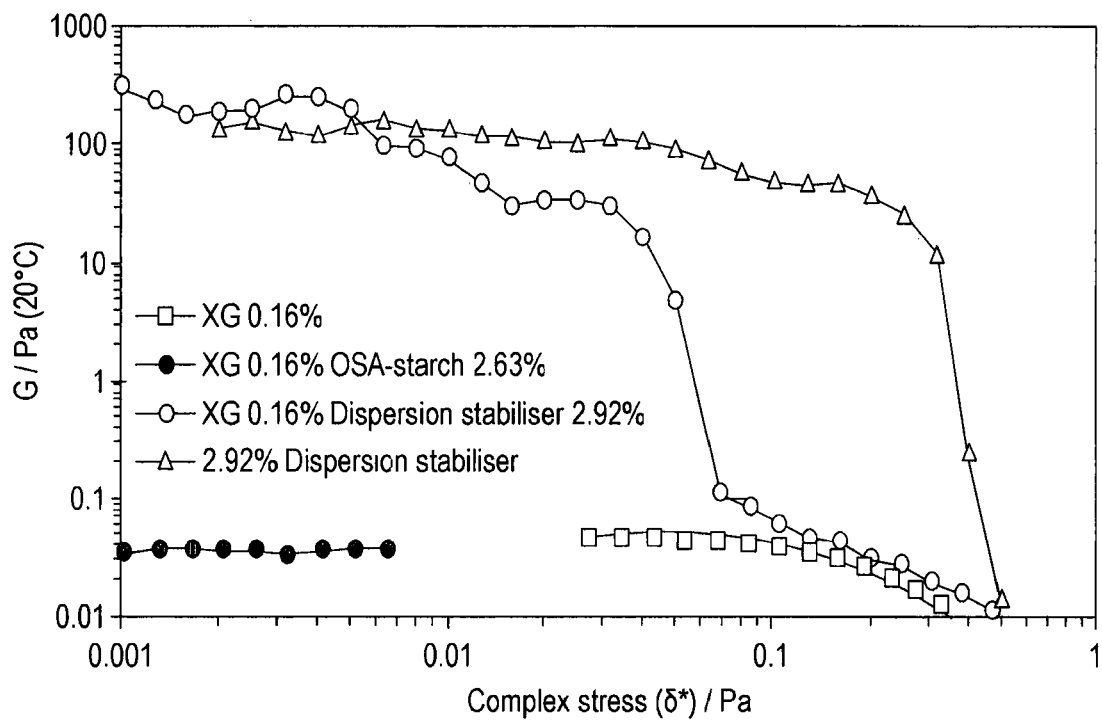
FIG. 22 shows the storage (elastic) modulus as a function of increasing stress of solutions containing combinations of xanthan (0.16% w/w), OSA-starch (2.63% w/w), and CB[n] (0.29% w/w), oscillatory flow at $1\ rad \cdot s^{-1}$.
Figure 23:
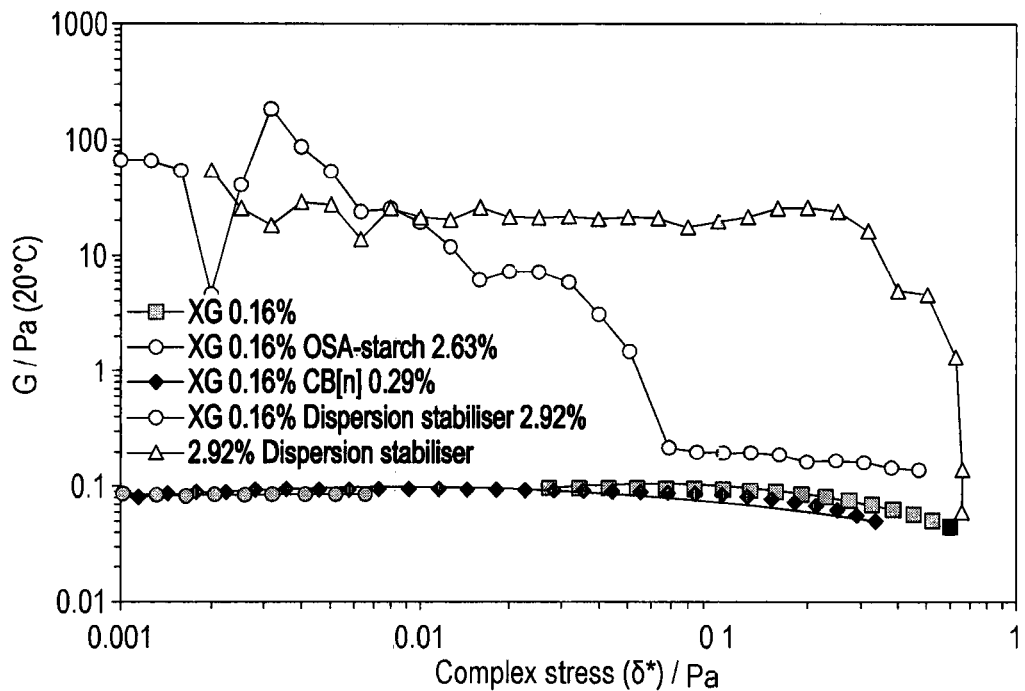
FIG. 23 shows the loss (viscous) modulus as a function of increasing stress of solutions containing combinations of xanthan (0.16% w/w), OSA-starch (2.63% w/w), and CB[n] (0.29% w/w), oscillatory flow at $1\ rad \cdot s^{-1}$.

The rheological behaviour of these samples was investigated in more detail in oscillatory flow mode. The data for 2.63% w/w OSA-starch is not shown because it behaves as a low-viscosity fluid and so does not give a meaningful, measurable elastic response in oscillatory flow. The first experiment involved oscillation at a constant frequency (1 rad·$s^{-1}$) at stepwise increasing stress. The resultant data are plotted as a function of complex (applied) stress σ*, in FIG. 22, the elastic (storage) modulus G' and in FIG. 23 the viscous (loss) modulus G". At low stress, the two samples that contain the dispersion stabiliser have significantly (approximately 1000×) higher values of the moduli and have G' larger than G". As stress is increased, there is a sharp fall in values of moduli (at 0.07 Pa for the xanthan/dispersion stabiliser and 0.32 Pa for the dispersion stabiliser). These results indicate that the dispersion stabiliser forms a weak network in solution that breaks or yields at a particular stress. This network requires both starch and CB[n] to be present and may occur even in the presence of xanthan gum.

Figure 24:
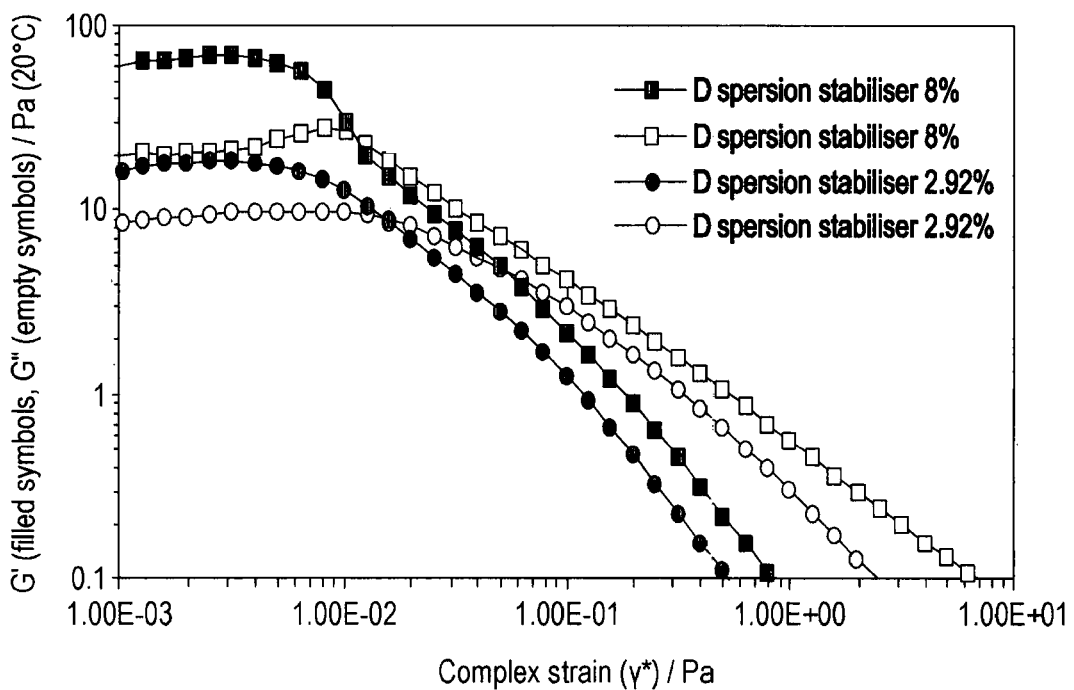
FIG. 24 shows the storage (filled symbols) and loss (empty symbols) moduli as a function of increasing strain of solutions of the dispersion stabiliser of the invention in oscillatory flow at $1\ rad \cdot s^{-1}$.

FIG. 24 shows that at strain of 5-10% the network has broken sufficiently that G' is not greater than G" at 1 rad·$s^{-1}$, i.e., at a lower strain than disclosed in WO 2013/124654 (Cambridge Enterprise Limited).

Figure 25:
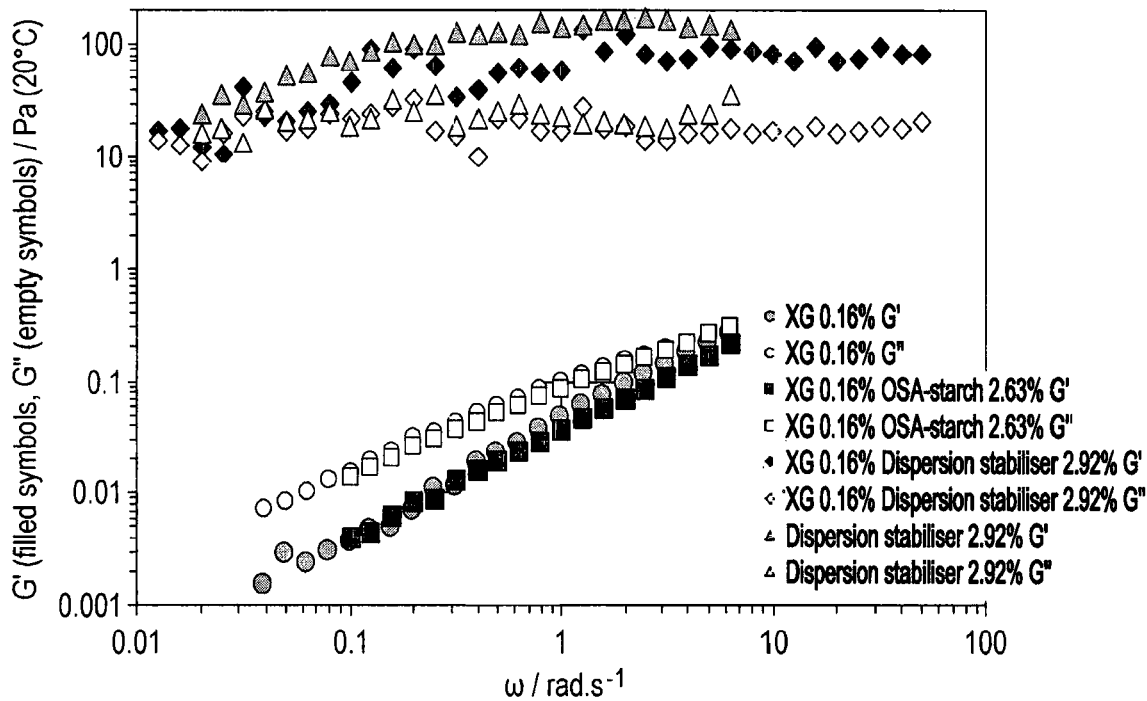
FIG. 25 shows the storage (filled symbols) and loss (open symbols) modulus as a function of decreasing frequency of solutions containing combinations of xanthan (0.16% w/w), OSA-starch (2.63% w/w), and CB[n] (0.29% w/w), oscillatory flow at low amplitude.

The frequency dependence of the response to low-amplitude (strain 0.0001 or stress 0.003 Pa) oscillatory flow for these samples is plotted in FIG. 25. The storage modulus is shown as filled symbols and the loss modulus as open symbols. The samples containing the dispersion stabiliser have a) higher moduli than the samples without, and b) values of storage modulus significantly higher than loss modulus at frequencies above 0.1 rad·$s^{-1}$, and c) the values of the moduli have relatively little frequency dependency, though the G' value gradually falls to that of the G" value near 0.01 rad·$s^{-1}$. Without the dispersion stabiliser, the loss modulus dominates below 6 rad·$s^{-1}$ and the values of moduli are strongly dependent on frequency. These data are consistent with the dispersion stabiliser-containing samples behaving as fragile gels with characteristic time approximately 100 s, while the combinations of xanthan and OSA-starch that do not contain CB[n] behave as viscoelastic fluids (relaxation time 0.1 s).

(d) Effect of Humectants on Rheology of the Dispersion Stabiliser Solution

Figure 26:
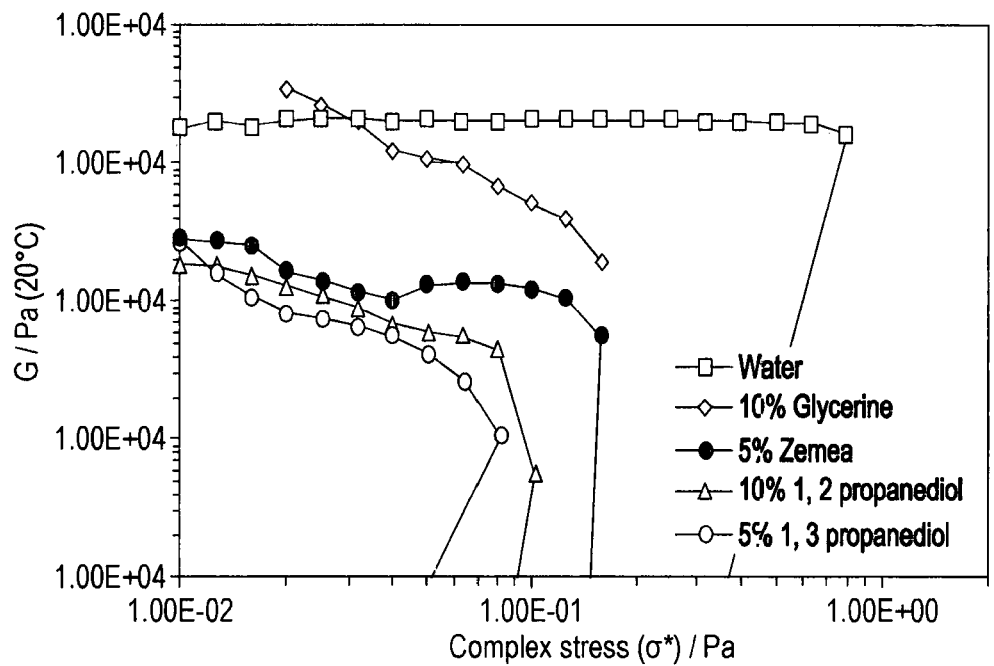
FIG. 26 shows the storage (elastic) modulus as a function of increasing stress of solutions containing 2.0% w/w dispersion stabiliser of the invention with different humectants, oscillatory flow at $1\ rad \cdot s^{-1}$.
Figure 27:
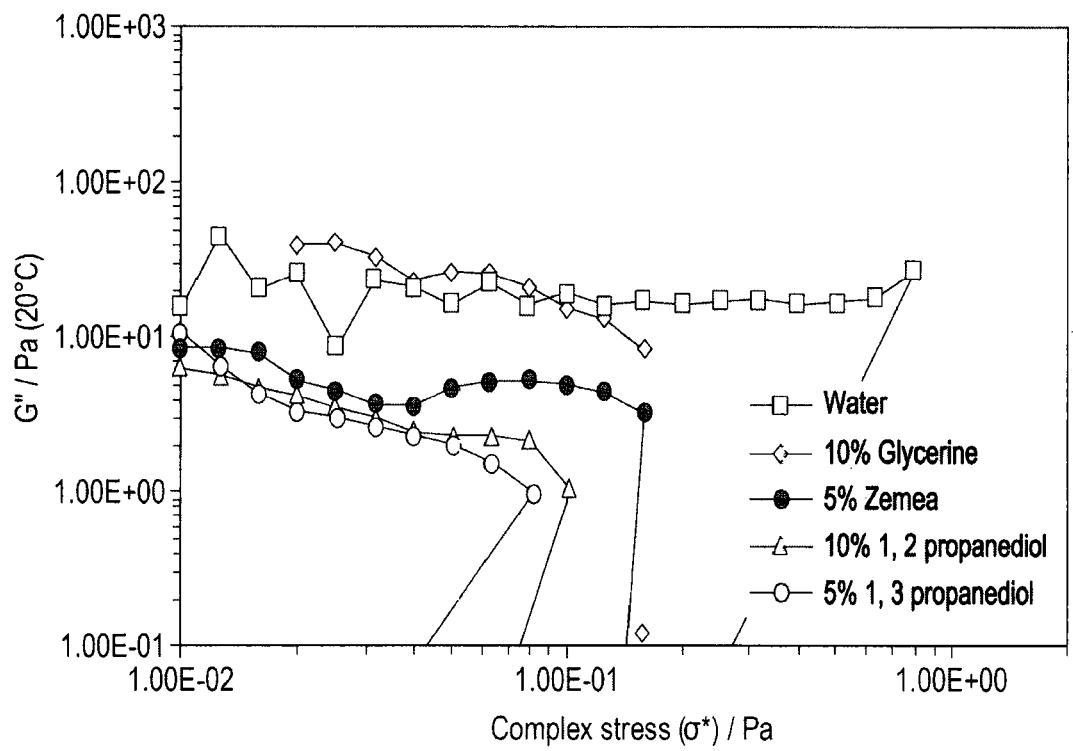
FIG. 27 shows the loss (viscous) modulus as a function of increasing stress of solutions containing 2.0% w/w dispersion stabiliser of the invention with different humectants, oscillatory flow at $1\ rad \cdot s^{-1}$.

A solution of 8% w/w dispersion stabiliser of the invention in 0.05% w/w potassium sorbate was prepared as described in Example 1. This solution was diluted in water and a humectant to produce 2% w/w dispersion stabiliser solutions. The humectants studied were glycerine, 1,2 propanediol and 1,3 propanediol. The effect of the humectants on structuring of the dispersion stabiliser solutions was investigated by rheological studies in oscillatory flow mode. Measurements at a constant frequency (1 rad·$s^{-1}$) at stepwise increasing stress are plotted as a function of complex (applied) stress. In FIG. 26, the elastic (storage) modulus and in FIG. 27 the viscous (loss) modulus.

At low stress, the samples have G' larger than G". As stress is increased, there is a sharp fall in values of moduli (at 0.1 Pa for the dispersion stabiliser samples with humectant). These results indicate that the dispersion stabiliser forms a weak network in solution that breaks or yields at a particular stress even in the presence of concentrations of humectants that may be found in personal care products.

EXAMPLE 10

The Effect of 60% v/v Oil on the Stability of an Oil-In-Water Emulsion Formed with the Emulsion Stabiliser of the Invention It is advantageous to be able to form stable emulsions with high oil content.

A solution of 2.6% w/w dispersion stabiliser was prepared by adding 20.8 g of OSA-starch (C*Emtex 12688 (Cargill)) to 800.0 g of water. The mixture was stirred for 2 hours and then heated at 80° C. for 2 hours. To this solution, 2.1 g of CB[8] was added to produce a 2.9% w/w solution of dispersion stabiliser.

The aqueous phase of Emulsion P consisted of 12.0 mL of the 2.9% w/w dispersion. The oil phase was 18.0 mL caprylyl methicone containing 0.02% w/v Oil Red O which was added to the aqueous phase and mixed at 2,500 rpm for 15 minutes on a Silverson L5 High Shear Laboratory Mixer with small head (a ⅝" micro general purpose disintegrating head) to form Emulsion P containing 1.1% w/w dispersion stabiliser.

The stability of the emulsion was monitored by visual inspection. Emulsion P showed no coalescence or creaming after 1 weeks storage at 20° C. Thus the dispersion stabiliser of the invention was able to emulsify an oil at 60% v/v.

EXAMPLE 11

The Effect of 75% v/v Oil on the Stability of an Oil-In-Water Emulsion Formed With the Emulsion Stabiliser of the Invention It is advantageous to be able to form stable emulsions with high oil content.

A solution of 10% w/w OSA-Starch was prepared by adding 80.0 g of OSA-starch to 800.0 g of water. The mixture was stirred for 2 hours and then heated at 80° C. for 2 hours to produce a 10.0% w/w solution of OSA-Starch.

A solution of 11% w/w dispersion stabiliser was prepared by adding 2.0 g CB[8] to 198.0 g of the 10% w/w OSA-starch solution described above.

The aqueous phase of Emulsion Q was prepared by combining 6.0 mL of the 11.0% w/w dispersion stabiliser with 1.5 mL of deionised water and mixing for 2 minutes at 1,000 rpm on a Silverson L5 High Shear Laboratory Mixer with small head (a ⅝" micro general purpose disintegrating head). The oil phase was 22.5 mL caprylyl methicone containing 0.02% w/v Oil Red O which was added to the aqueous phase and mixed at 2,500 rpm for 15 minutes to form Emulsion Q containing 2.2% w/w dispersion stabiliser.

The aqueous phase of Emulsion R was prepared by combining 6.0 mL of the 10.0% w/w OSA-starch with 1.5 mL of deionised water and mixing for 2 minutes at 1,000 rpm on a Silverson L5 High Shear Laboratory Mixer with small head (a ⅝" micro general purpose disintegrating head). The oil phase was 22.5 mL caprylyl methicone containing 0.02% w/v Oil Red O which was added to the aqueous phase and mixed at 2,500 rpm for 15 minutes. This sample containing 2.0% w/w OSA-Starch did not form a stable emulsion, with gross coalescence and oil separation observed within 2 hours.

The stability of Emulsion Q was monitored by visual inspection, showing no coalescence or creaming after 1 week of storage at 20° C. Thus the dispersion stabiliser of the invention was able to emulsify an oil at 75% v/v, whereas the OSA-starch alone was not able to form a stable emulsion.

EXAMPLE 12

The Effect of 75% v/v Oil on the Stability of an Oil-In-Water Emulsion Formed with the Emulsion Stabiliser of the Invention Present at Low Concentrations (0.7% w/w)

It is advantageous to be able to form stable emulsions with high oil content with a small amount of dispersion stabiliser containing a low ratio of cucurbituril: OSA-starch (1:100).

A solution of 10.1% w/w dispersion stabiliser was prepared by adding 0.2 g CB[8] to 199.8 g of the 10% w/w OSA-starch solution prepared in Example 11.

The aqueous phase of Emulsion S was prepared by combining 2.0 mL of the 10.1% w/w dispersion stabiliser with 5.6 mL of deionised water and mixing for 5 minutes at 1,000 rpm on a Silverson L5 High Shear Laboratory Mixer with small head (a ⅝" micro general purpose disintegrating head). The oil phase was 22.5 mL caprylyl methicone containing 0.02% w/v Oil Red O which was added to the aqueous phase and mixed at 2,500 rpm for 20 minutes to form Emulsion S containing 0.7% w/w dispersion stabiliser.

The stability of Emulsion S was monitored by visual inspection, showed no coalescence or creaming after 1 week of storage at 20° C. Thus the dispersion stabiliser of the invention was able to emulsify an oil at 75% v/v using a small amount of dispersion stabiliser which itself contained a low ratio of CB[8]:OSA-Starch (1:100).

EXAMPLE 13

The Effect of Cucurbituril to OSA-Starch Ratio on the Rheology/Network Properties of the Invention It is advantageous to be able to have the benefits of the invention with a wide range of ratios of cucurbiturils to OSA-starch.

The majority of previous examples have shown examples of the benefits of the invention at a ratio of cucurbituril to OSA-starch of 1:9. In this example, it is demonstrated that the benefits of the interaction of the cucurbituril with the OSA-starch can occur over a ratio of at least 0.003:0.997 to 0.13:0.87 (i.e. when cucurbituril is between 0.3 and 13% w/v of the dispersion stabiliser). This demonstration of the benefits via the rheology may be taken alongside Example 12 where enhanced emulsion stability is demonstrated at 1:99 cucurbituril to OSA-starch weight ratio.

Sample preparation: 6.00 g water was added to 4.00 g dispersion stabiliser and 0.025 g of potassium sorbate and a slurry formed by physical mixing. Then 40.0 g of water was added from a recently boiled kettle. This sample was sealed and placed in a water bath at 80° C. and stirred (magnetic bar) for 20 minutes and then allowed to cool to room temperature (20° C.). The total w/w content of dispersion stabiliser for all samples was 8.0%.

Rheological measurements were made with a Malvern Kinexus Pro+Rheometer with a 4° 40 mm diameter cone-plate stainless steel geometry with lightly roughened surfaces. The measurement temperature was 20° C. and samples were loaded with a Pasteur pipette before the cone was lowered to the correct position. After loading sample into the rheometer, it was typically sheared at 5 Pa for 1 minute then 0.01 Pa for one minute. The measurement procedure was to allow a thermal equilibration of two minutes before making two measurements consisting of first stepwise increasing stress in oscillatory flow at 1 rad·s⁻¹ then stepwise decreasing shear rate.

The stepwise sweep of increasing stress in oscillatory mode was from 0.001 to 1.0 Pa, with 10 points per decade. The solutions of dispersion stabiliser that have an interaction between the OSA-starch and the CB[n] should be elastic at low stress, i.e the elastic modulus is greater than the viscous modulus (G'>G"). The key parameter is when the applied stress at which the elastic strain (the product of the elastic modulus G' and the complex strain γ) is maximum. The yield strain is the strain at this maximum in the elastic stress. Solutions of OSA-starch of the type in this example have G">G', and are viscous to very low shear if they have been properly dissolved. The maximum value of the elastic modulus, which occurs below the yield stress, is also quoted as an indicator of the strength of any network.

dispersion stabiliser and that the viscosity for shear rates at or above 0.1 s⁻¹ does not exceed 6 Pa·s. At high shear, the dispersion stabiliser viscosity is very close to that of the parent OSA-starch viscosity, which can be a benefit in that the presence of the CB[n] does not negatively impact the flowability of the formulation in manufacturing process or application. The data in oscillatory flow show that for 8% dispersion stabiliser solutions containing 0.3 to 13% CB[n], the elastic modulus is greater than the storage modulus at low stress (and strain) and that there is a significant jump in strain (on increasing stress) at a strain value close to 1%, but below 2%. The strain immediately prior to this jump corresponds to the yield strain (and here the product of strain and elastic modulus is a maximum) and at higher strain, the loss modulus begins to become significantly larger than the elastic modulus.

Figure 31:
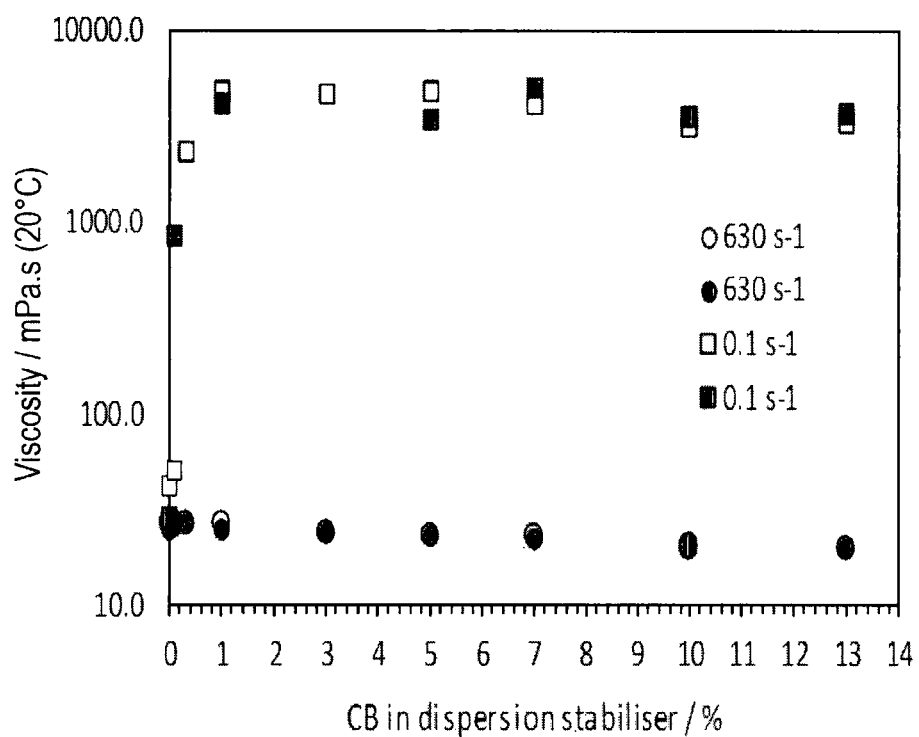
FIG. 31 shows the viscosity from a sweep of decreasing shear rates measured at 630 and $0.1 \cdot s^{-1}$.
Figure 32:
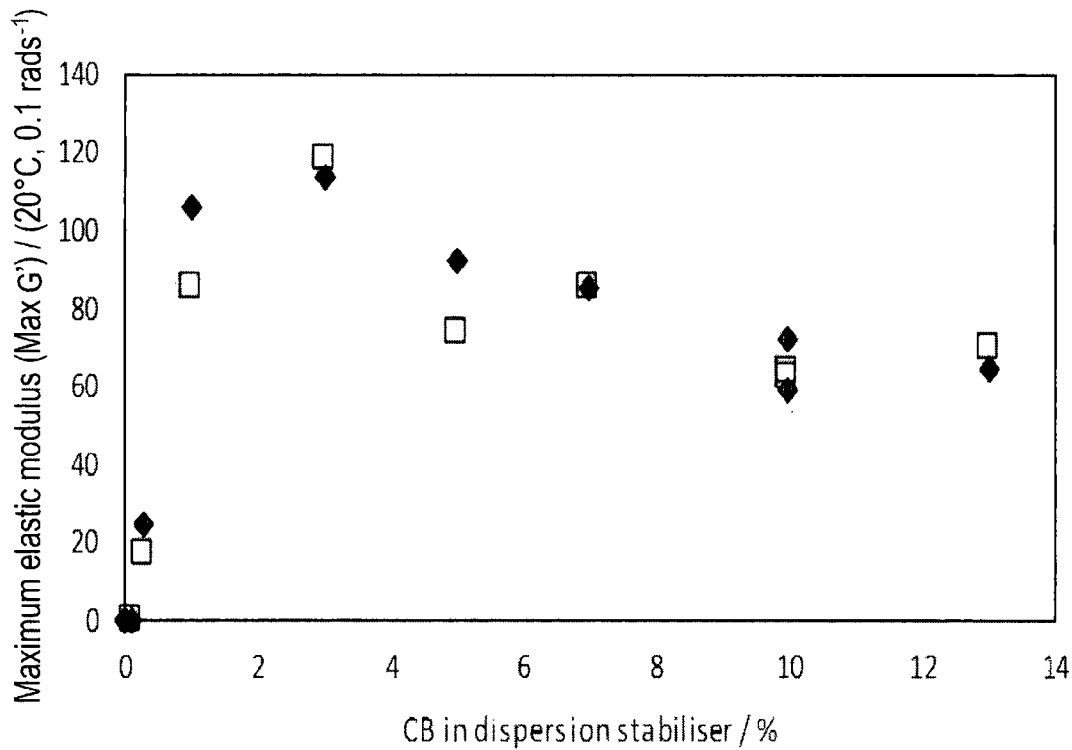
FIG. 32 shows the maximum value of the elastic modulus from a sweep of increasing stress from 0.001 to 1.0 Pa at $1\ rad \cdot s^{-1}$.
Figure 33:
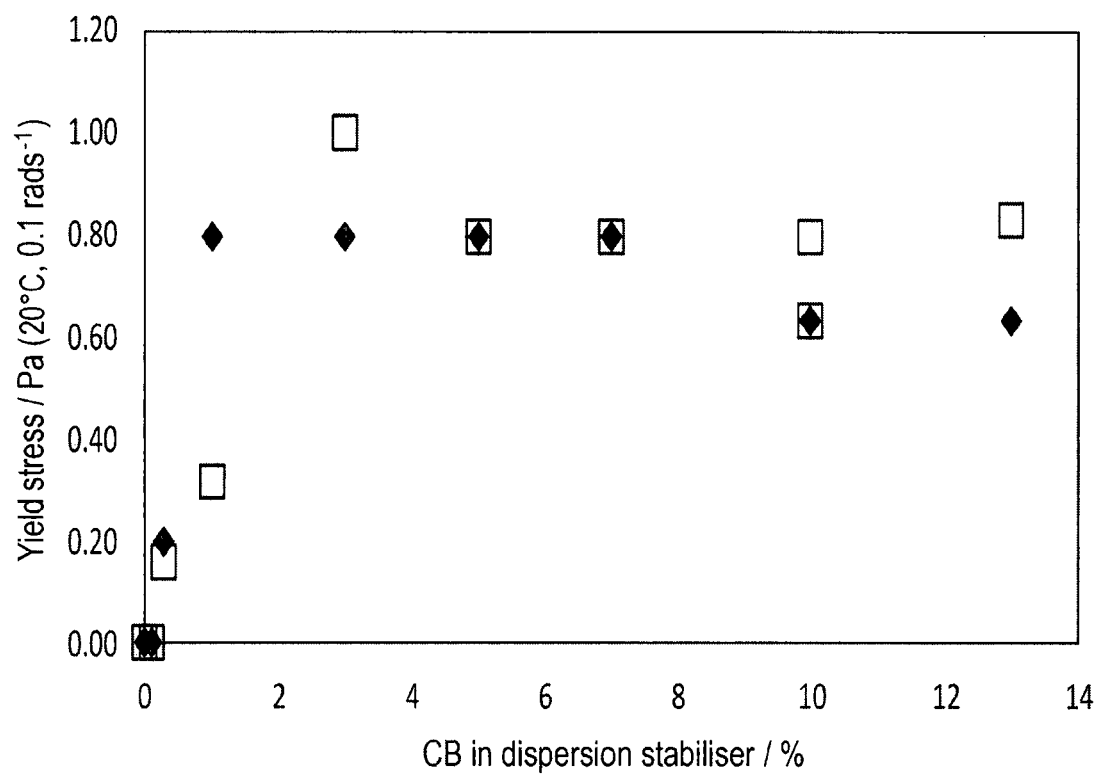
FIG. 33 shows the yield stress on a sweep of increasing stress from 0.001 to 1.0 Pa at $1\ rad \cdot s^{-1}$.

The key results from viscometry (viscosity at 0.1 and 630 s−1) and oscillation (maximum G' and yield stress) are summarised in Table 9 and FIGS. 31 to 33. At least one dataset was measured per composition.

TABLE 9

Summary of key parameters from rheological characterisation of 8% w/v solutions of dispersion stabiliser with different CB[n] levels and the parent OSA-starch.

| CB[n] in dispersion stabiliser (%) | η 630 s⁻¹ (mPa · s) | η 630 s⁻¹ (mPa · s) | η 630 s⁻¹ (mPa · s) | η 630 s⁻¹ (mPa · s) | Max G' (Pa) | Max G' (Pa) | Yield stress (Pa) | Yield stress (Pa) |
|---|---|---|---|---|---|---|---|---|
| 13 | 20.0 | 20.0 | 3259 | 3716 | 65 | 70 | 0.63 | 0.83 |
| 10 | 20.2 | 20.1 | 3235 | 3503 | 72 | 64 | 0.63 | 0.63 |
| 10 (3 mo. old) | 21.0 | 21.3 | 3237 | 3560 | 59 | 62 | 0.63 | 0.80 |
| 7 | 22.9 | 22.6 | 4095 | 5000 | 85 | 85 | 0.80 | 0.80 |
| 5 | 23.2 | 23.0 | 4890 | 3426 | 92 | 74 | 0.80 | 0.80 |
| 3 | 24.6 | 24.4 | 4700 | | 114 | 118 | 0.80 | 1.00 |
| 1 | 27.1 | 25.5 | 4740 | 4080 | 106 | 85 | 0.80 | 0.32 |
| 0.3 | 26.9 | 26.7 | 2332 | | 25 | 17 | 0.20 | 0.16 |
| 0.1 | 27.0 | 26.5 | 52.0 | 855 | 0.001 | 0.018 | 0.00 | 0.00 |
| 0 | 26.6 | 28.0 | 43.0 | 29.0 | 0.0003 | 0.0002 | 0.00 | 0.00 |
| 0 | 27.0 | 24.7 | | | 0.0003 | 0.0003 | 0.00 | 0.00 |

The second measurement in the sequence is determination of viscosity η at sweep of stepwise decreasing shear rates from 630 to 0.063 s⁻¹ with 5 points per decade. The dispersion stabiliser solutions will show a consistently increasing shear viscosity as the rate falls below 100 s⁻¹ if there is a weak network formed because of interactions between the OSA-starch and the CB[n]. This viscosity rise is also shown as a plateauing in the shear stress (here typically between 0.3 and 0.6 Pa) at a low shear rate (rather than continuing to decrease). A correctly dissolved OSA-starch solution should be Newtonian, with stress falling to below 0.01 Pa as shear rate decreases.

In these studies, three compositions of dispersion stabiliser powder were prepared by mixing OSA-starch and CB[n] with CB[n] levels to 7, 10 and 13% w/w CB[n]. A batch of dispersion stabiliser with 10% CB[n] that had been prepared 3 months previously was included in the study. Mixtures of the 8% OSA-starch solution and the 8% dispersion stabiliser at 7% CB[n] (in the dispersion stabiliser) were prepared to give 8% w/w solutions of dispersion stabiliser containing from 5 to 0.1% w/w CB[n] (i.e 95 to 99.9% OSA-starch). Each composition was studied at least once, and repeat experiments are reported amongst the results summary graphs and in Table 9.

Figure 28:
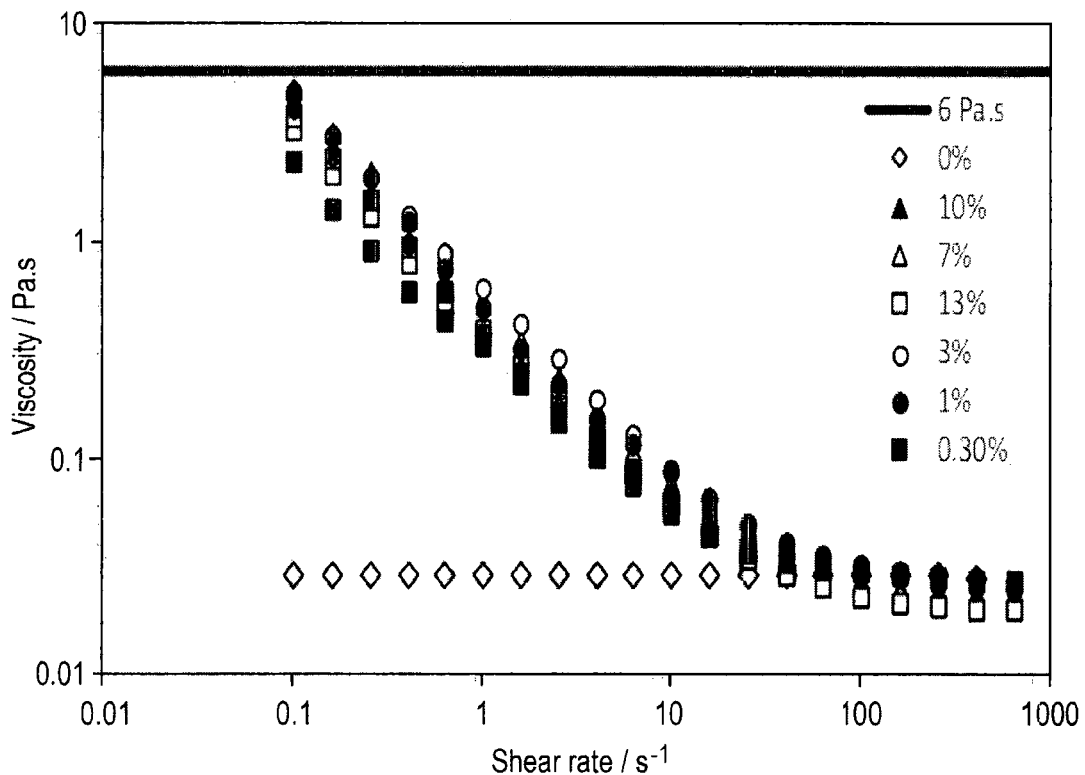
FIG. 28 shows the shear viscosity on decreasing rate from 630 to $0.1\ s^{-1}$ with the thick line drawn at 6 Pa·s. for solutions of OSA-starch and dispersion stabiliser at 8% w/w and cucurbituril content of the 8% solids ranging from 0 to 13% w/w.
Figure 29:
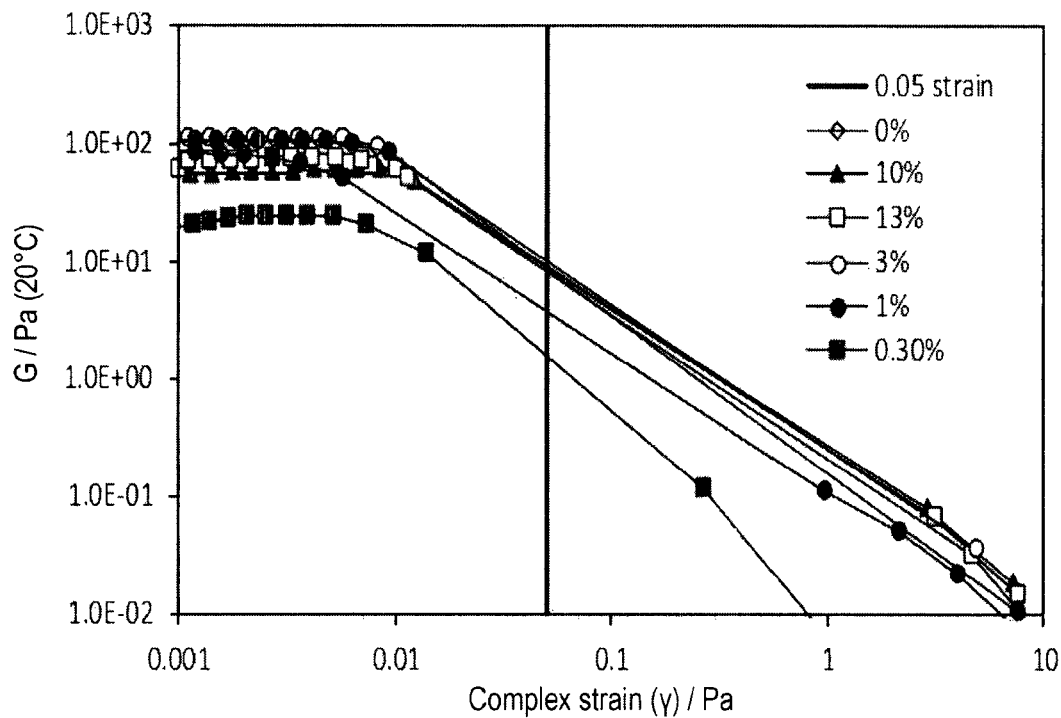
FIG. 29 shows the elastic/storage modulus on increasing stress from 0.001 to 1.0 Pa shown as a function of shear strain from 0.1 to 1000% at $1\ rad \cdot s^{-1}$ with the maximum in elastic modulus of the OSA-starch solution below 0.0003 Pa (below 10% of the loss modulus, G') and so off scale and solutions of OSA-starch and dispersion stabiliser at 8% w/w and cucurbituril content of the 8% w/w solids ranging from 0 to 13% w/w.
Figure 30:
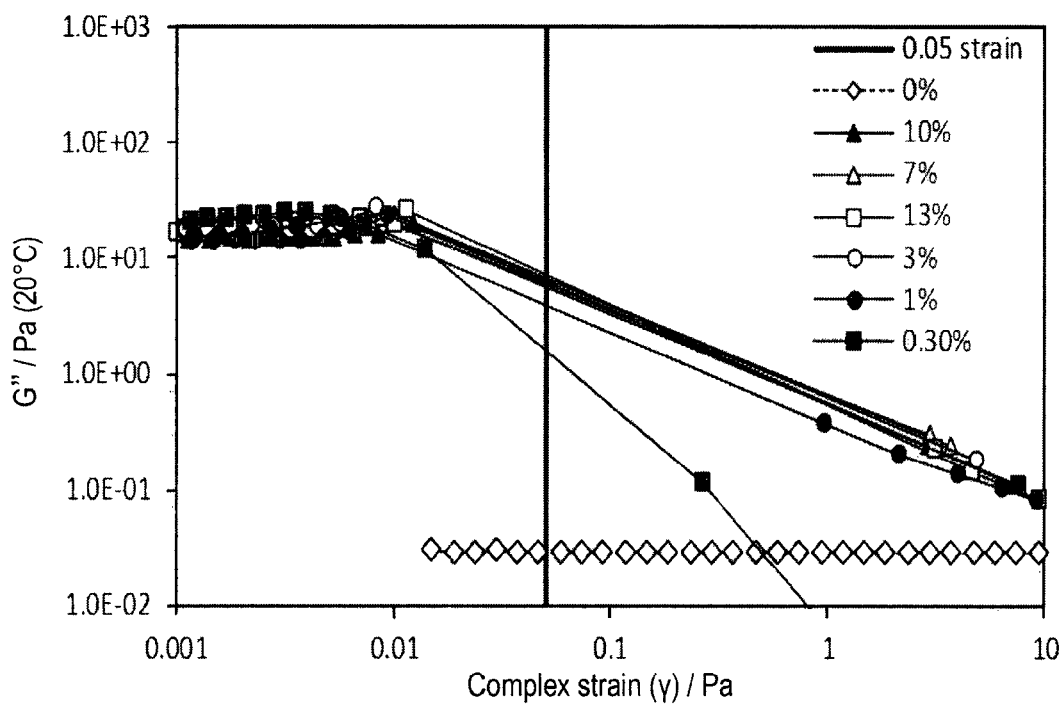
FIG. 30 shows the viscous/loss modulus on increasing stress from 0.001 to 1.0 Pa shown as a function of shear strain from 0.1 to 1000% at $1\ rad \cdot s^{-1}$ with solutions of OSA-starch and dispersion stabiliser at 8% w/w and cucurbituril content of the 8% w/w solids ranging from 0 to 13% w/w.

Results for a range of compositions are shown for viscometry (FIG. 28) and oscillation (FIG. 29, G' and FIG. 30, G"). In viscometry, it is clear that the data are very similar for a wide range (at least 0.3 to 13%) of CB[n] levels in the This data (and others here) show that the yield strain (above which G" dominates G') is much lower for this invention (below 2% shown) than in WO 2013/124654 A1 (Cambridge Enterprise Limited) (5-10%). In addition, the viscosity at 0.1 s⁻¹ is below 6 Pa·s, so at least 10× lower than in WO 2013/124654 A1 (Cambridge Enterprise Limited). This low value of the viscosity at 0.1 s⁻¹ occurs over a wide range of dispersion stabiliser concentrations (3-33%) in the Examples here. Furthermore, in contrast to the hydrogels of WO 2013/124654 A1 (Cambridge Enterprise Limited), in this invention, cucurbituril does not transform OSA-starch solutions from free flowing liquids to gels that can support their own weight.

EXAMPLE 14

Broad Spectrum Protection Tinted Moisturizer/BB Cream/Liquid Foundation

The invention provides the basis for high-performance cosmetic products. This formulation is an example of an oil-in-water emulsion applies smoothly and evenly. It contains pigmented products. The white 'background' pigment is replaced by UVA light-protecting mineral particles, which provide protection from UVA radiation that causes the skin to look older, wrinkled, and discoloured. In addition, it contains iron oxide pigments for coloration. The look produced after application is sheer, with fine lines diminished. In this case, the invention is included in the formulation via both water and oil phases.

| Phase | % | Tradename | INCI | Supplier | Function |
|---|---|---|---|---|---|
| A | 33.7% | Water | | | Solvent |
| B | 25.0% | Solaveil XT-40 | Titanium Dioxide (and) Aqua (and) Polyglyceryl-2 Caprate (and) Sucrose Stearate (and) *Simmondsia Chinensis* (Jojoba) Seed Oil (and) Stearic Acid (and) Alumina (and) Glyceryl Caprylate (and) Squalane | Croda | Active, Sunscreen |
| B | 1.5% | Dispersion stabiliser of the invention | 9:1 w/w OSA-starch:CB[n] | | Emulsifier |
| B | 15.0% | Zemea | Propanediol | DuPont Tate & Lyle | Humectant |
| B | 3.0% | (Tan pigment blend) | Iron oxides | | Color |
| B | 1.0% | Sensiva PA 40 | Phenylpropanol (and) Propanediol (and) Caprylyl Glycol (and) Tocopherol | Schuelke | Preservative |
| B | 0.3% | Keltrol CG | Xanthan Gum | CPKelco | Polymer |
| C | 15.0% | SustOleo MCT | Isostearyl Isostearate | Inolex | Emollient |
| C | 2.5% | Crodacol C70 | Cetyl Alcohol | Croda | Thickener |
| C | 1.5% | Dispersion stabiliser of the invention | 9:1 w/w OSA-starch:CB[n] | | Emulsifier |
| C | 0.5% | Esterlac Care+ | Sodium Isostearoyl Lactylate | Corbion | Emulsifier |
| C | 1.0% | Staramic 747 | Corn Starch Modified | Tate & Lyle | Polymer |

Procedure:
1) Preheat water to 80° C.
2) Premix B as a slurry, then add to A with propeller stirring
4) Heat C to 75° C.
5) Add C with propeller stirring
5) Homogenize until appearance is glossy The resultant emulsion is a cosmetic cream in which the solids are well suspended and spreads to provide even coverage on the skin. Further, since there are no hydrophilic surfactants in this formulation, the disruption of the barrier lipid bilayers is of no concern and skin wear resistance should be increased. The formulation provides a makeup base, with sun protection (anti-aging) and attractive tint.

EXAMPLE 15

Inorganic Sunscreen Cream

This example describes an emulsion suitable for use as a sunscreen. It contains inorganic sunscreen particles in both oil and water phases. The particles provide protection against UVA and UVB radiation. Again, the invention is included in the formulation via both water and oil phases.

| Phase | % | Tradename | INCI | Supplier | Function |
|---|---|---|---|---|---|
| A | 56.7% | Water | | | Solvent |
| A | 1.5% | Dispersion stabiliser of the invention | 9:1 w/w OSA-starch:CB[n] | | Emulsifier |
| B | 15.0% | Zemea | Propanediol | DuPont Tate & Lyle | Humectant |
| B | 1.0% | Sensiva PA 30 | Propanediol (and) Phenylethyl Alcohol (and) Undecyl Alcohol (and) Tocopherol | Schuelke | Preservative |
| B | 0.3% | Keltrol CG | Xanthan Gum | CPKelco | Polymer |
| B | 5.0% | Solaveil XT-40W | Titanium Dioxide (and) Aqua (and) Polyglyceryl-2 Caprate (and) Sucrose Stearate (and) *Simmondsia Chinensis* (Jojoba) Seed Oil (and) Stearic Acid (and) Alumina (and) Glyceryl Caprylate (and) Squalane | Croda | Active, Sunscreen |
| C | 15.0% | Solaveil CT-300 | Caprylic/Capric Triglyceride (and) Titanium Dioxide (and) Polyhydroxystearic Acid (and) Aluminum Stearate (and) Alumina | Croda | Active, Sunscreen |
| C | 2.5% | Esterlac Smooth | Glyceryl Stearate | Corbion | Thickener |
| C | 1.5% | Dispersion stabiliser of the invention | 9:1 w/w OSA-starch:CB[n] | | Emulsifier |
| C | 0.5% | Esterlac Care + | Sodium Isostearoyl Lactylate | Corbion | Emulsifier |
| C | 1.0% | Staramic 747 | Corn Starch Modified | Tate & Lyle | Polymer |

Procedure:
1) Preheat water to 80° C.
2) Premix B, then add to A with propeller stirring
3) Heat C to 75° C.
4) Add C with propeller stirring
5) Homogenize until appearance is glossy After application, the skin is left feeling moisturized but not greasy. This formulation is transparent on the skin, and is appropriate for daily wear, or while at the beach or playing outdoor sports. The rheology offers shear-thinning behaviour with a slight degree of elasticity, which is not only appealing aesthetically to a wide range of consumers, but also should lead to films on the skin that are relatively thick yet consistent, as required for maximum utilization of sunscreen actives. Further, since there are no hydrophilic surfactants in this formulation, the resistance to wash-off should be excellent.

EXAMPLE 16

The Effect of the Cucurbituril to OSA-Starch Ratio on the Stability of an Oil-In-Water Emulsion Formed with the Emulsion Stabiliser of the Invention It is advantageous to be able to have the benefits of the invention with a wide range of ratios of cucurbiturils to OSA-starch.

Dispersion stabiliser (a blend of 9:1 w/w OSA-starch:CB[n]) was prepared by mixing 1800 g of OSA-starch and 200 g of CB[n] in a Hobart HSM20 mixer equipped with a 20 L bowl using a B-beater blade for 15 minutes.

The aqueous phase of Emulsion T was prepared by combining 3.63 g of OSA-starch with 1.09 g xanthan gum (Jungbunzlauer) in 18.17 g glycerol (Alfa Aesar) before adding to 260.70 g recently boiled deionised water and stirring for 15 minutes at 400 rpm with a propeller stirrer. 19.37 g of deionised water was added to account for the 19.35 g which was lost during heating and a sample of 10.03 g was taken. The oil phase was prepared by heating 3.50 g of OSA-starch in 70.18 g caprylic/capric triglyceride (Crodamol GTCC, Croda) to 75° C. and stirring for 15 minutes. The oil phase was added to the aqueous phase and stirred for 5 minutes at 400 rpm before mixing at 3,000 rpm on a Silverson L5 high shear mixer with a standard emulsor screen for 5 minutes to form Emulsion T containing 2% w/w OSA-starch. The emulsion was stirred for 1 hour 12 minutes before 3.35 g phenoxyethanol (Acros Organics) was added. The emulsion was stirred for a further 15 minutes.

The aqueous phase of Emulsion U was prepared by combining 1.81 g of the dispersion stabiliser prepared above with 1.82 g OSA-starch and 1.09 g xanthan gum (Jungbunzlauer) in 18.15 g glycerol (Alfa Aesar) before adding to 260.53 g recently boiled deionised water and stirring for 15 minutes at 400 rpm with a propeller stirrer before adding 28.41 g of deionised water to account for water lost due to evaporation and removing a sample of 10.37 g. The oil phase was prepared by heating 1.75 g of the dispersion stabiliser prepared above and 1.75 g of OSA-starch in 70.06 g caprylic/capric triglyceride (Crodamol GTCC, Croda) to 75° C. and stirring for 15 minutes. The oil phase was added to the aqueous phase and stirred for 5 minutes at 400 rpm before mixing at 3,000 rpm on a Silverson L5 high shear mixer with a standard emulsor screen for 5 minutes to form Emulsion U containing 2% w/w dispersion stabiliser comprising 9.5:0.5 OSA-starch:CB[n]. The emulsion was stirred for 1 hour 15 minutes before 3.34 g phenoxyethanol (Acros Organics) was added. The emulsion was stirred for a further 15 minutes.

The aqueous phase of Emulsion V was prepared by combining 3.63 g of the dispersion stabiliser prepared above with 1.09 g xanthan gum (Jungbunzlauer) in 18.15 g glycerol (Alfa Aesar) before adding to 260.74 g recently boiled deionised water and stirring for 15 minutes at 400 rpm with a propeller stirrer. 19.79 g of deionised water was added to account for the 19.72 g which was lost during heating and a sample of 10.07 g was taken. The oil phase was prepared by heating 3.50 g of the dispersion stabiliser prepared above in 70.03 g caprylic/capric triglyceride (Crodamol GTCC, Croda) to 75° C. and stirring for 15 minutes. The oil phase was added to the aqueous phase and stirred for 5 minutes at 400 rpm before mixing at 3,000 rpm on a Silverson L5 high shear mixer with a standard emulsor screen for 5 minutes to form Emulsion V containing 2% w/w dispersion stabiliser comprising 9:1 OSA-starch:CB[n]. The emulsion was stirred for 1 hour 17 minutes before 3.29 g phenoxyethanol (Acros Organics) was added. The emulsion was stirred for a further 15 minutes.

Emulsions T-V were stored at rest in a 45° C. oven and monitored by visual inspection to determine emulsion stability. The data is summarised in Table 10 wherein the quoted percentage is the emulsion height relative to the total sample height.

Emulsions U and V showed less creaming and greater resistance to creaming and coalescence at 45° C. than emulsion T. Thus the dispersion stabiliser of the invention with a range of CB[n] loadings was able increase emulsion stability compared to OSA-starch.

TABLE 10

Visual observations for Emulsions T-V stored at rest at 45° C. The quoted percentage is the emulsion height relative to the total sample height.

| Emulsion | | Visual observations when stored at 45° C. (emulsion height relative to the total sample height (%)) | | | | |
|---|---|---|---|---|---|---|
| | | 0 weeks | 1 week | 2 weeks | 3 weeks | 4 weeks |
| T | 2% w/w OSA-starch | 100 | 38 | 36 | 34 | 0 |
| U | 2% w/w dispersion stabiliser (9.5:0.5 OSA-starch:CB[n]) | 100 | 88 | 67 | 60 | 48 |
| V | 2% w/w dispersion stabiliser (9:1 OSA-starch:CB[n]) | 100 | 91 | 72 | 60 | 47 |

EXAMPLE 17

The Effect of the Cucurbituril to OSA-Starch Ratio Using an Alternative OSA-Starch on the Stability of an Oil-In-Water Emulsion Formed with the Emulsion Stabiliser of the Invention It is advantageous to be able to have the benefits of the invention with a range of OSA-starches and with a range of ratios of cucurbiturils to OSA-starch. In this example the OSA-starch is C*EmTex 12688 from Cargill. The emulsions were prepared in the same manner as described in Example 16 except that xanthan gum was not included.

Emulsions X-Z were stored at rest in a 45° C. oven and monitored by visual inspection to determine emulsion stability. The data is summarised in Table 11 wherein the quoted percentage is the emulsion height relative to the total sample height.

Emulsions X, Y and Z showed less creaming and greater resistance to coalescence at 45° C. than emulsion W. Thus the dispersion stabiliser of the invention with a range of CB[n] loadings was able increase emulsion stability compared to OSA-starch.

TABLE 11

Visual observations for Emulsions W-Z stored at rest at 45° C. The quoted percentage is the emulsion height relative to the total sample height.

| Emulsion | | Visual observations when stored at 45° C. (emulsion height relative to the total sample height (%)) | | | | | |
|---|---|---|---|---|---|---|---|
| | | 0 weeks | 1 week | 2 weeks | 4 weeks | 8 weeks | 12 weeks |
| W | 2% w/w OSA-starch | 100 | 97 | 67 | 0 | | |
| X | 2% w/w dispersion stabiliser (9.8:0.2 OSA-starch:CB[n]) | 100 | 99 | 71 | 60 | 48 | 47 |
| Y | 2% w/w dispersion stabiliser (9.5:0.5 OSA-starch:CB[n]) | 100 | 97 | 88 | 69 | 53 | 47 |
| Z | 2% w/w dispersion stabiliser (9:1 OSA-starch:CB[n]) | 100 | 100 | 97 | 70 | 54 | 48 |

EXAMPLE 18

The Effect of the Cucurbituril to OSA-Starch Ratio Using an Alternative OSA-Starch on the Stability of an Oil-In-Water Emulsion Formed with the Emulsion Stabiliser of the Invention It is advantageous to be able to have the benefits of the invention with a range of OSA-starches and with a wide range of ratios of cucurbiturils to OSA-starch. In this example the OSA-starch is MiraMist 662 from Tate & Lyle. The emulsions were prepared in the same manner as described in Example 16.

Samples of Emulsions AA-AC were stored at rest in a 45° C. oven and were monitored by visual inspection to determine emulsion stability. The data are summarised in Table 12 wherein the quoted percentage is the emulsion height relative to the total sample height.

Emulsions AB and AC showed less creaming and greater resistance to coalescence at 45° C. than emulsion AA. Thus the dispersion stabiliser of the invention with a range of CB[n] loadings was able to increase emulsion stability compared to OSA-starch.

TABLE 12

Visual observations for Emulsions AA-AC stored at rest at 45° C. The quoted percentage is the emulsion height relative to the total sample height.

| Emulsion | | Visual observations when stored at 45° C. (emulsion height relative to the total sample height (%)) | | | | |
|---|---|---|---|---|---|---|
| | | 0 weeks | 1 week | 2 weeks | 4 weeks | 8 weeks |
| AA | 2% w/w OSA-starch | 100 | 53 | 46 | 40 | 0 |
| AB | 2% w/w dispersion stabiliser (9.5:0.5 OSA-starch:CB[n]) | 100 | 87 | 64 | 50 | 44 |
| AC | 2% w/w dispersion stabiliser (9:1 OSA-starch:CB[n]) | 100 | 100 | 100 | 95 | 92 |

EXAMPLE 19

The Effect of the Emulsion Stabiliser on the Stability of an Oil-In-Water Emulsion Compared to Gum Acacia at Multiple Concentrations of Emulsion Stabiliser It is advantageous to be able to have the benefits of the invention with a range of macromolecular amphiphilic emulsifiers and at a range of dose levels. In this example the macromolecular amphiplilic emulsifier was Gum Arabic (also known as Gum Acacia) (KLTA-AMF from Kerry).

The aqueous phase of Emulsion AD was prepared by combining 3.63 g of gum acacia with 1.09 g xanthan gum (Jungbunzlauer) in 18.17 g glycerol (Alfa Aesar) before adding to 264.20 g recently boiled deionised water and stirring for 15 minutes at 400 rpm with a propeller stirrer. 15.62 g of deionised water was added to account for the 15.80 g which was lost during heating and a sample of 10.00 g was taken. The oil phase was prepared by heating 70.01 g caprylic/capric triglyceride (Crodamol GTCC, Croda) to 75° C. and stirring for 15 minutes. The oil phase was added to the aqueous phase and stirred for 5 minutes at 400 rpm before mixing at 3,000 rpm on a Silverson L5 high shear mixer with a standard emulsor screen for 4 minutes 30 seconds to form Emulsion AD containing 1% w/w gum acacia. The emulsion was stirred for 1 hour before 3.14 g phenoxyethanol (Acros Organics) was added. The emulsion was stirred for a further 15 minutes before mixing on a Silverson L5 high shear mixer at 3,000 rpm with a standard emulsor screen for 30 seconds.

The aqueous phase of Emulsion AE was prepared by combining 3.27 g of gum acacia, 0.36 g of CB[n] with 1.09 g xanthan gum (Jungbunzlauer) in 18.13 g glycerol (Alfa Aesar) before adding to 264.01 g recently boiled deionised water and stirring for 15 minutes at 400 rpm with a propeller stirrer. 16.23 g of deionised water was added to account for the 16.56 g which was lost during heating and a sample of 10.16 g was taken. The oil phase was prepared by heating 70.04 g caprylic/capric triglyceride (Crodamol GTCC, Croda) to 75° C. and stirring for 15 minutes. The oil phase was added to the aqueous phase and stirred for 5 minutes at 400 rpm before mixing at 3,000 rpm on a Silverson L5 high shear mixer with a standard emulsor screen for 4 minutes 30 seconds to form Emulsion AE containing 1% w/w dispersion stabiliser comprising 9:1 gum acacia:CB[n]. The emulsion was stirred for 1 hour before 3.16 g phenoxyethanol (Acros Organics) was added. The emulsion was stirred for a further 15 minutes before mixing on a Silverson L5 high shear mixer at 3,000 rpm with a standard emulsor screen for 30 seconds.

The aqueous phase of Emulsion AF was prepared by combining 7.25 g of gum acacia with 1.09 g xanthan gum (Jungbunzlauer) in 18.12 g glycerol (Alfa Aesar) before adding to 260.35 g recently boiled deionised water and stirring for 15 minutes at 400 rpm with a propeller stirrer. 14.07 g of deionised water was added to account for the 13.97 g which was lost during heating and a sample of 10.00 g was taken. The oil phase was prepared by heating 70.02 g caprylic/capric triglyceride (Crodamol GTCC, Croda) to 75° C. and stirring for 15 minutes. The oil phase was added to the aqueous phase and stirred for 5 minutes at 400 rpm before mixing at 3,000 rpm on a Silverson L5 high shear mixer with a standard emulsor screen for 4 minutes 30 seconds to form Emulsion AH containing 2% w/w gum acacia. The emulsion was stirred for 1 hour before 3.14 g phenoxyethanol (Acros Organics) was added. The emulsion was stirred for a further 15 minutes before mixing on a Silverson L5 high shear mixer at 3,000 rpm with a standard emulsor screen for 30 seconds.

The aqueous phase of Emulsion AG was prepared by combining 6.53 g of gum acacia, 0.72 g of CB[n] with 1.09 g xanthan gum (Jungbunzlauer) in 18.17 g glycerol (Alfa Aesar) before adding to 260.36 g recently boiled deionised water and stirring for 15 minutes at 400 rpm with a propeller stirrer. 15.84 g of deionised water was added to account for the 15.81 g which was lost during heating and a sample of 10.02 g was taken. The oil phase was prepared by heating 70.02 g caprylic/capric triglyceride (Crodamol GTCC, Croda) to 75° C. and stirring for 15 minutes. The oil phase was added to the aqueous phase and stirred for 5 minutes at 400 rpm before mixing at 3,000 rpm on a Silverson L5 high shear mixer with a standard emulsor screen for 4 minutes 30 seconds to form Emulsion AG containing 2% w/w dispersion stabiliser comprising 9:1 gum acacia:CB[n]. The emulsion was stirred for 1 hour before 3.15 g phenoxyethanol (Acros Organics) was added. The emulsion was stirred for a further 15 minutes before mixing on a Silverson L5 high shear mixer at 3,000 rpm with a standard emulsor screen for 30 seconds.

Samples of Emulsions AD-AG were stored at rest in a 45° C. oven and were monitored by visual inspection to determine emulsion stability. The data is summarised in Table 13 wherein the quoted percentage is the emulsion height relative to the total sample height.

Emulsion AE showed less creaming at 45° C. than emulsion AD. Similarly, emulsion AG showed less creaming at 45° C. than emulsion AF. Thus the dispersion stabiliser of the invention was able increase emulsion stability compared to gum acacia at a range of concentrations.

TABLE 13

Visual observations for Emulsions AD-AG stored at rest at 45° C. The quoted percentage is the emulsion height relative to the total sample height.

| | | Visual observations when stored at 45° C. (emulsion height relative to the total sample height (%)) | | | | |
|---|---|---|---|---|---|---|
| Emulsion | | 0 weeks | 1 week | 2 weeks | 4 weeks | 8 weeks |
| AD | 1% w/w Gum Arabic | 100 | 97 | 88 | 63 | 48 |
| AE | 1% w/w dispersion stabiliser (9:1 OSA-starch:CB[n]) | 100 | 97 | 91 | 78 | 65 |

TABLE 13-continued

Visual observations for Emulsions AD-AG stored at rest at 45° C. The quoted percentage is the emulsion height relative to the total sample height.

| Emulsion | | Visual observations when stored at 45° C. (emulsion height relative to the total sample height (%)) | | | | |
|---|---|---|---|---|---|---|
| | | 0 weeks | 1 week | 2 weeks | 4 weeks | 8 weeks |
| AF | 2% w/w Gum Arabic | 100 | 100 | 99 | 96 | 91 |
| AG | 2% w/w dispersion stabiliser (9:1 OSA-starch:CB[n]) | 100 | 100 | 100 | 100 | 98 |

The invention claimed is:

1. A dispersion stabiliser precursor composition comprising one or more of cucurbituril, a variant or a derivative thereof, and one or more oil-in-water macromolecular amphiphilic emulsifier, wherein
the dispersion stabiliser precursor composition is in the form of a free flowing powder.

2. An oil-in-water emulsion composition comprising one or more of cucurbituril, a variant or a derivative thereof, and one or more oil-in-water macromolecular amphiphilic emulsifier.

3. The dispersion stabiliser precursor composition according to claim 1, wherein the cucurbituril is selected from the group consisting of CB[5], CB[6], CB[7], CB[8], CB[9], CB[10], CB[11] CB[12], CB[13], CB[14] and mixtures thereof.

4. The dispersion stabiliser precursor composition according to claim 1, wherein the oil-in-water macromolecular amphiphilic emulsifier is a hydrophobically-modified polysaccharide.

5. The dispersion stabiliser precursor composition according to claim 4, wherein the hydrophobically-modified polysaccharide is a polysaccharide which has been modified by reaction with $C_1$-$C_{22}$ alkyl- or a $C_3$-$C_{22}$ alkenyl-succinic anhydride.

6. The dispersion stabiliser precursor composition according to claim 4, wherein the hydrophobically-modified polysaccharide is a hydrophobically-modified branched polysaccharide, the branched polysaccharide is selected from the group consisting of starch, amylopectin, dextrin, gum Arabic, and mixtures thereof.

7. The dispersion stabiliser precursor composition according to claim 1, wherein the weight ratio of one or more of cucurbituril, a variant or a derivative thereof to one or more oil-in-water macromolecular amphiphilic emulsifier is 1:1000 to 1:5.

8. The dispersion stabiliser precursor composition according to claim 1, substantially free of a first surfactant which is water-soluble and/or has an HLB value of at least 12.

9. The dispersion stabiliser precursor composition according to claim 1 comprising a second surfactant which is oil-soluble and/or has an HLB value of 1-10.

10. The dispersion stabiliser precursor composition according to claim 9, wherein the second surfactant is selected from the group consisting of sorbitan monolaurate, sodium isostearoyl lactylate, an alkali metal salt of stearoyl lactylate, and mixtures thereof.

11. The dispersion stabiliser precursor composition according to claim 9, wherein the second surfactant is in the range 0.001-5% w/v of an oil-in-water emulsion composition comprising the dispersion stabiliser precursor composition or the oil-in-water emulsion composition.

12. The oil-in-water emulsion composition according to claim 2 comprising 0.01-30% w/w combination of one or more of cucurbituril, a variant or a derivative thereof, and one or more oil-in-water macromolecular amphiphilic emulsifier.

13. The oil-in-water emulsion composition according to claim 2 comprising 1-90% v/v an oil phase.

14. The oil-in-water emulsion composition according to claim 13, wherein the oil phase is in the form of droplets of d90 0.1-1000 microns in diameter.

15. The oil-in-water emulsion composition according to claim 2 which is a personal care composition.

16. A method for preparing an oil-in-water emulsion composition according to claim 2, the method comprising the steps of:
(a) preparing an aqueous phase;
(b) preparing an oil phase;
(c) combining the aqueous and oil phases under shear;
wherein the one or more of cucurbituril, a variant or a derivative thereof, and one or more oil-in-water macromolecular amphiphilic emulsifier is added to the oil phase and/or the aqueous phase.

17. The method for preparing an oil-in-water emulsion composition according to claim 16, wherein the second surfactant is added to the oil phase and/or the aqueous phase.

18. A method comprising applying the dispersion stabiliser precursor composition according to claim 1 for stabilising an oil-in-water emulsion.

* * * * *